US012778434B2

(12) United States Patent
Wu et al.

(10) Patent No.: US 12,778,434 B2
(45) Date of Patent: Nov. 3, 2026

(54) METHOD AND DEVICE FOR NON-INVASIVE DETECTION OF CENTRAL ARTERIAL PRESSURE AND OTHER INTRALUMINAL LARGE ARTERIAL PRESSURES

(71) Applicant: SHENZHEN RAYCOME HEALTH TECHNOLOGY CO., LTD., Shenzhen (CN)

(72) Inventors: Xiaoguang Wu, Shenzhen (CN); Zihuan Wu, Shenzhen (CN)

(73) Assignee: SHENZHEN RAYCOME HEALTH TECHNOLOGY CO., LTD., Shenzhen (CN)

( * ) Notice: Subject to any disclaimer, the term of this patent is extended or adjusted under 35 U.S.C. 154(b) by 179 days.

(21) Appl. No.: 18/856,677

(22) PCT Filed: Apr. 13, 2022

(86) PCT No.: PCT/CN2022/086663
§ 371 (c)(1),
(2) Date: Oct. 14, 2024

(87) PCT Pub. No.: WO2023/197214
PCT Pub. Date: Oct. 19, 2023

(65) Prior Publication Data

US 2025/0255497 A1 Aug. 14, 2025

(51) Int. Cl.
*A61B 5/021* (2006.01)
*A61B 5/00* (2006.01)
(Continued)

(52) U.S. Cl.
CPC ...... *A61B 5/02116* (2013.01); *A61B 5/02125* (2013.01); *A61B 5/02233* (2013.01);
(Continued)

(58) Field of Classification Search
CPC .... A61B 5/021–02125; A61B 5/02141; A61B 5/022–0235; A61B 5/7225; A61B 5/7242
See application file for complete search history.

(56) References Cited

U.S. PATENT DOCUMENTS 5,095,912 A 3/1992 Tomita
5,423,324 A * 6/1995 Tomita .............. A61B 5/02208 600/494
(Continued)

FOREIGN PATENT DOCUMENTS

CA 2235339 A1 4/1997
CN 101912259 B 10/2012
(Continued)

*Primary Examiner* — Adam J Eiseman
(74) *Attorney, Agent, or Firm* — Bayramoglu Law Offices LLC

(57) ABSTRACT

Provided are method and device for non-invasive detection of central arterial pressure and other intraluminal large arterial pressures. Blood flow and vascular elasticity are the main factors affecting pulse waveform acquisition. A mid-stream airbag strap can be positioned at the same level as an intraluminal large artery in a human body, and an upstream signal channel can be positioned close to the trunk of the human body and thus is very close to the intraluminal large artery so that the influence of the vascular elasticity is minimized. On the basis of the relationship between the pressure in a blood vessel and the pressure of the airbag strap outside the blood vessel under the condition that the width of the midstream airbag strap is sufficient.

10 Claims, 8 Drawing Sheets

(51) Int. Cl.
*A61B 5/022* (2006.01)
*A61B 5/0225* (2006.01)
*A61B 5/0235* (2006.01)

(52) U.S. Cl.
CPC .......... *A61B 5/0225* (2013.01); *A61B 5/0235* (2013.01); *A61B 5/7225* (2013.01); *A61B 5/7242* (2013.01)

(56) References Cited

U.S. PATENT DOCUMENTS

| | | | | |
|---|---|---|---|---|
| 7,780,605 | B2 * | 8/2010 | Yamashita | A61B 5/02141 600/490 |
| 9,072,436 | B2 * | 7/2015 | Kobayashi | A61B 5/021 |
| 2015/0025399 | A1 * | 1/2015 | Nishibayashi | A61B 5/02116 600/492 |
| 2016/0310021 | A1 * | 10/2016 | Kato | A61B 5/7225 |
| 2016/0360982 | A1 * | 12/2016 | Ohno | A61B 5/742 |
| 2022/0015652 | A1 * | 1/2022 | Lee | A61B 5/02233 |

FOREIGN PATENT DOCUMENTS

| | | | |
|---|---|---|---|
| CN | 103070678 | A | 5/2013 |
| CN | 103479343 | A | 1/2014 |
| CN | 104159503 | A | 11/2014 |
| CN | 113925478 | A | 1/2022 |
| JP | 2006311951 | A | 11/2006 |
| JP | 2011520502 | A | 7/2011 |
| JP | 2013183814 | A | 9/2013 |
| KR | 102374437 | B1 | 3/2022 |
| RU | 2742453 | C1 | 2/2021 |
| WO | 2015122191 | A1 | 8/2015 |
| WO | 2022059653 | A1 | 3/2022 |

* cited by examiner

METHOD AND DEVICE FOR NON-INVASIVE DETECTION OF CENTRAL ARTERIAL PRESSURE AND OTHER INTRALUMINAL LARGE ARTERIAL PRESSURES

CROSS-REFERENCE TO THE RELATED APPLICATIONS

This application is the national phase entry of International Application No. PCT/CN2022/086663, filed on Apr. 13, 2022.

TECHNICAL FIELD

The present invention relates to blood pressure measurement, in particular to method and device for non-invasive measurement of central arterial pressure and other intraluminal large arterial pressures.

BACKGROUND

ESC-ESH Guidelines for the Management of Arterial Hypertension 2003 pointed out: Central arterial pressure is different from brachial arterial pressure. Compared with brachial arterial blood pressure measurement, which is frequently used in daily clinical practice, central arterial blood pressure is more closely related to organs such as the heart, brain and kidneys and their complications. It has a unique and higher value in the prediction of cardiovascular diseases and related complications. Central arterial pressure refers to the lateral pressure borne on the blood vessel at the root of the ascending aorta. Theoretically, central arterial pressure is more closely related to target organ damage and cardiovascular diseases and has a higher value in prediction of cardiovascular events than peripheral brachial arterial pressure, which has been proved in some clinical trials. Researches have demonstrated that central arterial pressure (aortic pressure) has a higher value in clinical prediction than peripheral arterial pressure (brachial arterial pressure). Therefore, it is of great significance to measure central arterial blood pressure.

Central arterial blood pressure measurement methods can be categorized into non-invasive measurement methods and invasive measurement methods, depending on whether they are invasive or not. An invasive catheter method can be used to measure central arterial blood pressure. With that method, a left cardiac catheter is used to directly measure the blood pressure at the root of the ascending aorta, and, at the same time, the blood pressure is converted into readable data by a pressure transducer, and a central arterial blood pressure waveform is recorded continuously, which can accurately reflect central arterial blood pressure. The invasive catheter method is the most accurate method for measuring central arterial blood pressure. Although invasive central arterial blood pressure measurement is considered a gold criterion for central arterial blood pressure measurement, its wide clinical application is limited because of its invasive nature, high cost and difficult operation.

Non-invasive central arterial blood pressure measurement is a measurement method that is easier to practice. At present, commonly used instruments for non-invasive measurement of central arterial blood pressure mainly obtain central arterial pressure with a non-invasive method, such as planar pulse wave analysis for carotid artery and radial artery or diastolic wave analysis for carotid artery, including: (1) substitution method: a carotid arterial pressure wave is used as an approximate substitute for the ascending aortic pressure wave, but it can't be measured directly with a sphygmomanometer; (2) visual observation method: the ascending aortic pressure is analyzed by visually observing delayed systolic waveform changes of a radial arterial pressure wave; this method is a semi-quantitative method in nature; (3) synthesis method: the ascending aortic pressure is synthesized from a radial arterial pressure wave, i.e., a radial arterial pulse wave is recorded non-invasively with an arterial pulse wave analyzer using a contact pressure probe, and converted into a central arterial pulse wave through computer processing. However, all three methods described above have a severe defect of high measurement error.

SUMMARY

An object of the present invention is to provide a novel method for non-invasive detection of central arterial pressure and other intraluminal arterial pressures so as to realize accurate measurement of central arterial pressure and other intraluminal arterial pressures.

Another object of the present invention is to provide a novel device for non-invasive detection of central arterial pressure and other intraluminal arterial pressures, so as to realize accurate measurement of central arterial pressure and other intraluminal arterial pressures.

Yet another object of the present invention is to provide a three-channel pulse wave signal sensor, which can accurately measure central arterial pressure and other intraluminal arterial pressures.

In the present application, an electronic signal sensor refers to an electrokinetic transducer for converting a pulse wave signal to be measured in a channel into an electronic signal, except for inflatable airbags, including but not limited to a pressure sensor and a photoelectric sensor.

Central arterial pressure refers to the lateral pressure borne on the blood vessel at the root of the ascending aorta. According to the human body structure, the left subclavian artery of the human body originates from the ascending aorta, extends to an axillary artery, and then extends to a brachial artery, forming a continuous arterial duct. Although there are several different arterial branches originating from this continuous arterial duct at other positions, most of the arterial branches belong to smaller arterial vessels. A relatively large branch among the arterial branches is the left vertebrobasilar artery, which is connected to the upper wall of an initial segment of the left subclavian artery. Therefore, when the blood vessel of the brachial artery in the left arm is blocked, and the blood pressure measurement position on the left arm is at the same level as the ascending aorta, the pressure felt at the blood pressure measurement position on the left arm is equivalent to the pressure at the junction between the upper wall of the initial segment of the left subclavian artery and the left vertebrobasilar artery. Besides, owing to the fact that the first segment of the left subclavian artery has a large inner diameter and a short length, the blood flow rate there is not high. Therefore, when the first segment of the left subclavian artery is not seriously blocked, the flow resistance in this segment is not high, and the resultant pressure difference is not significant. Therefore, it can be concluded that when the blood vessel of the brachial artery in the left arm is blocked and the blood pressure measurement position on the left arm is at the same level as the ascending aorta, the blood pressure at the blood pressure measurement position on the left arm is equivalent to the pressure at the junction between one end of the left subclavian artery and the ascending aorta, which, by definition, is the central arterial pressure.

If the first segment of the left subclavian artery is seriously blocked, the blood pressure measurement can be performed on the right arm as an alternative. The right subclavian artery originates from the brachiocephalic trunk. When the brachial artery in the right arm is blocked, and the blood pressure measurement position on the right arm is at the same level as the ascending aorta, the blood pressure at the blood pressure measurement position on the right arm is equivalent to the pressure at the junction between one end of the right subclavian artery and the brachiocephalic trunk, which is close to the central arterial pressure, but there will be some measurement error. Although the central arterial pressure that can be measured by means of the right arm has some error, the blood pressure measured by means of the right arm is actually the innominate arterial pressure, but it is very close to the central arterial pressure.

In addition to the central arterial pressure, there are other intraluminal arterial pressures, including the aforementioned innominate arterial pressure, abdominal aorta terminal pressure, etc. Here, "intraluminal" means "intra-abdominal" or "intrathoracic". The blood pressure measured by means of the right arm is actually the blood pressure of the innominate artery, and the blood pressure measured by means of a lower limb is actually the blood pressure at the terminal of the abdominal aorta. The inventive technique in the present invention not only can measure the central arterial pressure, but also can measure other intraluminal large arterial pressures. The technique not only can measure the blood pressure by means of an upper limb, but also can measure the blood pressure by means of a lower limb.

In order to accurately measure the central arterial pressure and other intraluminal arterial pressures, firstly, the acquired pulse wave should be as close as possible to the waveform of the central artery or other intraluminal arteries. Blood flow and vascular elasticity are the main factors that affect pulse waveform acquisition. Therefore, During the acquisition of the waveform of central arterial pressure or other intraluminal arterial pressures, the acquisition position should be as close as possible to the ascending aorta or other intraluminal arteries, and the arterial blood flow should be blocked at the same time. Secondly, the position where the pulse waveform is acquired should be as close as possible to the position where the brachial arterial blood pressure or femoral arterial blood pressure is measured.

The device in the present invention comprises a three-channel pulse wave signal sensor, two-way air valves, a linear air valve, an air pump, pressure sensors, signal amplifiers, a microprocessor, a display unit, a keyboard, etc. The microprocessor is connected with pulse wave signal analog-to-digital converters (ADCs), or pulse wave signal ADCs are directly integrated in the microprocessor.

The three-channel pulse wave signal sensor has three signal channels, which are designated as an upstream signal channel, a midstream signal channel and a downstream signal channel, according to the blood flow direction. The midstream signal channel is an inflatable airbag which can block arterial blood flow when inflated. The width of the airbag for the midstream signal channel is the same as the width of the airbag used in the traditional Korotkoff sound method, and the minimum width is determined according to the circumference of the measured limb of the subject. The upstream signal channel and the downstream signal channel are pressure sensors or photoelectric sensors, or may be designed as inflatable airbags. The spacing distances among the upstream signal channel, the midstream signal channel and the downstream signal channel are designed according to the length of the measured limb of the subject. The three signal channels may be closely connected into an integral structure or spaced by certain distances according to the specific requirement of use. Preferably, the spacing distance between the upstream signal channel and the midstream signal channel is set to 0-15 cm; preferably, the spacing distance between the midstream signal channel and the downstream signal channel is set to 0-30 cm.

In the case that the upstream signal channel and the downstream signal channel are inflatable airbags, the upstream airbag is connected to a first two-way air valve through a tube and is connected to a first pressure sensor through a tube at the same time. The midstream airbag is connected to a second two-way air valve through a tube and is connected to a microporous air valve through a tube at the same time, and the microporous air valve is connected to the downstream airbag through a tube. The downstream airbag is connected to a third two-way air valve through a tube, and is connected to the second pressure sensor and the other end of the microporous air valve through a tube.

The other ends of the three two-way air valves are connected together through tubes and are connected to the third pressure sensor, the air pump and the linear air valve through tubes. The three pressure sensors are respectively connected to the signal amplifiers through electric wires, and the output terminals of the signal amplifiers are connected to the input terminals of the three ADCs of the microprocessor through electric wires. The microprocessor is connected to the display unit and the keyboard, and to the three two-way air valves, the three pressure sensors, the linear air valve and the air pump through electric wires.

In order to better describe the measurement process and calculation method in the present invention, corresponding times and variables are defined as follows.

A time period in which the inflated pressure of the midstream airbag is much higher than the systolic pressure of the brachial artery and the blood flow in the brachial artery is completely blocked is referred to as a completely blocked time zone $t_x$.

A time period in which the midstream airbag gradually deflates till the downstream signal sensor begins to generate several pulse wave signals after the midstream airbag is inflated and blocks the blood flow in the brachial artery is referred to as a semi-blocked time zone $t_y$.

In the semi-blocked time zone $t_y$, the downstream signal channel begins to generate pulse wave signals. The moment of the upstroke of the downstream pulse wave signal is referred to as time $t_I$.

After the midstream airbag is inflated and blocks the blood flow in the brachial artery, the pressure variation of the midstream airbag can reflect the variation of the blood volume in the brachial artery. In the time period in which the pulse signal at the time $t_I$ is generated, a second derivative of the curve of the air pressure in the midstream blocking airbag within a time interval from the upstroke of the midstream pulse wave to the time $t_I$ is calculated to obtain a brachial arterial blood flow acceleration curve, and a first zero-crossing point from positive to negative in the acceleration curve is found out, and is referred to as time $t_{II}$.

A delay time $\Delta t$ from the upstroke of the midstream pulse wave to the time $t_{II}$ in a pulse cycle in the semi-blocked time zone $t_y$ is measured, and then a moment delayed from the upstroke of the upstream pulse wave by the delay time $\Delta t$ in a pulse cycle in the completely blocked time zone $t_x$ is calculated, and referred to as time $t_{III}$.

The idea of measuring the central arterial pressure and other intraluminal arterial pressures in the present invention is as follows:

1. In the case that the width of the midstream airbag strap is sufficient, at the moment of the upstroke of the downstream pulse wave, the blood pressure in the brachial artery or femoral artery at the position of the midstream airbag strap is equal to the pressure of the midstream airbag strap.
2. In the semi-blocked state, at the moment of the upstroke of the downstream pulse wave, the blood flow rate is equal to zero, and the blood pressure in the brachial artery or femoral artery at the upstream position is equal to the blood pressure in the brachial artery at the position of the midstream airbag strap. Thus, it is equal to the pressure of the midstream airbag strap. It is not equal to the pressure of the midstream airbag strap at any other time.
3. In the semi-blocked state, the moment when the blood flow acceleration is zero is calculated according to the midstream pressure curve. Then, the blood pressure in the brachial artery or femoral artery at the upstream position at the moment when the blood flow acceleration is zero is calculated, according to the upstream pressure curve and the blood pressure in the brachial artery at the upstream position at the moment of the upstroke of the downstream pulse wave. Here, a point where the acceleration is zero is found.
4. According to the delay time of the point where the acceleration is zero in the semi-blocked state, a moment with the same delay time in the completely blocked state is found. At that moment, the blood pressure in the brachial artery or femoral artery at the upstream position is equal to the blood pressure in the brachial artery at the upstream position at the moment when the acceleration is zero in the semi-blocked state.
5. According to the upstream pressure curve in the completely blocked state and the blood pressure in the brachial artery at the upstream position at the moment when the acceleration is zero in the completely blocked state, a maximum blood pressure of the brachial artery or femoral artery at the upstream position in the completely blocked state is calculated, which is the systolic pressure of the central artery or other intraluminal large arteries.
6. Owing to the fact that the blood flow rate is close to zero at diastolic pressure, the diastolic pressure of the central artery or other intraluminal large arteries is approximately equal to the diastolic pressure of the brachial artery or femoral artery.

The measurement process is described below in an example of blood pressure measurement with a three-channel pulse wave signal sensor having upstream and downstream channels formed from airbags:

Step 1: (In general, the first step is not indispensable) Open the two-way air valve connected to the midstream airbag, close the linear air valve, and start the air pump to inflate the midstream airbag via the two-way air valve, and inflate the downstream airbag via the microporous air valve at the same time, while detecting and acquiring the pressure fluctuation signals of the downstream airbag, till the blood flow in the brachial artery is stopped, i.e., the pulse wave signal of the downstream airbag is zero. Open the two-way air valve connected to the midstream airbag, and gradually open the linear air valve so that the midstream airbag gradually deflates, the blood in the brachial artery gradually flows, and pulse wave signals begin to appear in the downstream signal channel; log the amplitudes of several pulse wave signals appearing initially in the downstream signal channel, log the air pressure of the midstream airbag at each pulse synchronously, and perform linear fitting between them to calculate a corresponding air pressure of the midstream airbag when the amplitude of the pulse wave signal of the downstream signal channel crosses zero; that air pressure is the systolic pressure of the brachial artery. As the midstream airbag continues deflating, measure a time delay between the air pressure fluctuation signal of the midstream airbag and the pulse wave signal of the downstream signal channel, perform fitting and calculate a time point when the time delay gradually decreases to a constant value; the air pressure of the midstream airbag at this moment is the diastolic pressure of the brachial artery. For the calculation method for judging brachial arterial blood pressure according to pulse amplitude and time delay, please see Chinese Patent No. ZL201010247968.6 titled "Non-Invasive Blood Pressure Measurement Device" and published as Chinese Patent Publication No. CN101912259B, which is granted to the first inventor, Wu Xiaoguang, of the present application. The entire content of the Chinese Patent No. CN101912259B is incorporated herein.

Step 2: Start the air pump to inflate the upstream airbag to tens of millimeters of mercury via the two-way air valve (if the Step 1 is performed, pressurize the upstream airbag to about the diastolic pressure of the brachial artery measured in the Step 1). From now on, acquire the pulse wave signals of the upstream and downstream signal channels and the air pressure signal of the midstream airbag synchronously, till the measurement is finished.

Step 3: Start the air pump to inflate the midstream airbag via the two-way air valve, inflate the downstream airbag via the microporous air valve at the same time, and detect and acquire the pulse wave signal of the downstream airbag synchronously till the blood flow in the brachial artery is stopped, i.e., the pulse wave signal of the downstream airbag is zero. At this moment, the air pressure of the midstream airbag is approximately equal to the systolic pressure of the brachial artery. Continue inflating the midstream airbag so that the air pressure of the midstream airbag is greater than the systolic pressure of the brachial artery, for example, by 10-100 mmHg typically.

Step 4: Close all air valves, stop the inflation of the midstream airbag, and wait for several heartbeat cycles; the current state is a completely blocked state. The waiting period is referred to as a completely blocked time zone $t_x$.

Step 5: Open the two-way air valve connected to the midstream airbag, and gradually open the linear air valve, so that the midstream airbag gradually deflates, the blood in the brachial artery gradually flows, and pulse wave signals begin to appear in the downstream signal channel; the current state is a semi-blocked state, and this time period is referred to as a semi-blocked time zone $t_y$. Log the amplitudes of several pulse wave signals appearing initially in the downstream signal channel, log the air pressure of the midstream airbag at each pulse synchronously, and perform linear fitting between them to calculate a corresponding air pressure of the midstream airbag when the amplitude of the pulse wave signal of the downstream signal channel crosses zero; that air pressure is the systolic pressure of the brachial artery. As the midstream airbag continues deflating, measure a time delay between the air pressure fluctuation signal of the midstream airbag and the pulse wave signal of the downstream signal channel, perform fitting and calculate a time point when the time delay gradually decreases to a constant value; the air pressure of the midstream airbag at this moment is the diastolic pressure of the brachial artery. The diastolic pressure of the brachial artery is used to calculate the systolic pressure of the central artery.

Step 6: Calculate the systolic pressure and diastolic pressure of the central artery, according to the pulse wave signals of the upstream and downstream signal channels, the air pressure signal of the midstream airbag and the diastolic pressure of the brachial artery that are acquired synchronously in the above process. Now, the measurement is finished.

The central arterial pressure can be calculated through five steps, according to the pulse wave signal data of the upstream, midstream, and downstream channels, as well as the air pressures in the upstream and midstream airbags that are acquired with the above method.

The steps of the method in the present invention and the meanings of the parameters can be understood with reference to FIGS. 8-11.

For the convenience of description, relevant variables are defined as follows.

$P_C$ is the central arterial blood pressure, $P_{CS}$ is the systolic pressure of the central artery, $P_{CII}$ and $P_{CIII}$ are the central arterial blood pressures at the time $t_{II}$ and $t_{III}$ respectively, and $P_{Cd}$ is the diastolic pressure of the central artery.

$P_1$ is the blood pressure in the brachial artery at the position of the upstream signal channel, $P_{1I}$, $P_{1II}$ and $P_{1III}$ are the blood pressures in the brachial artery at the position of the upstream signal channel at the time $t_I$, $t_{II}$ and $t_{III}$ respectively, $P_{1s}$ is the maximum value of the blood pressure in the brachial artery at the position of the upstream signal channel in a pulse cycle where t is located in the completely blocked time zone $t_x$, and $P_d$ is the diastolic pressure of the brachial artery at the position of the upstream signal channel. $H_1$ is the signal intensity at the position of the upstream signal channel or the air pressure in the upstream airbag, $H_{1I}$, $H_{1II}$ and $H_{1III}$ are the signal intensities at the position of the upstream signal channel or the air pressures in the upstream airbag at the time $t_I$, $t_{II}$ and $t_{III}$ respectively, and $H_{1s}$ is the maximum value of the signal intensity at the position of the upstream signal channel or the air pressure in the upstream airbag in a pulse cycle where $t_1$ is located in the completely blocked time zone $t_x$.

$H_d$ is the signal amplitude of the upstream signal channel at diastolic pressure. $P_2$ is the blood pressure in the brachial artery at the position of the midstream airbag, $P_{2I}$ and $P_{2II}$ are the blood pressures in the brachial artery at the position of the midstream airbag at the time $t_I$ and $t_{II}$ respectively, $H_2$ is the air pressure in the midstream airbag, and $H_{2I}$ and $H_{2II}$ are the air pressures in the midstream airbag at the time $t_I$ and $t_{II}$ respectively.

$P_{2d}$ is the diastolic pressure of the brachial artery at the position of the midstream signal channel. Owing to the fact the blood in the brachial artery doesn't flow when it is at diastolic pressure, the diastolic pressure of the brachial artery at the position of the upstream signal channel is equal to the diastolic pressure of the brachial artery at the position of the midstream airbag, i.e., $P_d=P_{2d}$.

Owing to the fact that the blood in the brachial artery doesn't flow at the moment of diastolic pressure, and the measuring airbag is kept at the same level as the ascending aorta during the measurement, the diastolic pressure $P_d$ measured at the position of the brachial artery is the diastolic pressure of the central artery, i.e., $P_{Cd}=P_d=P_{2d}$.

The specific calculation steps are as follows:

Step 1: In the semi-blocked time zone $t_y$, the downstream signal sensor begins to generate pulse wave signals; the air pressure in the midstream blocking airbag at the moment of the upstroke of the pulse wave signal (i.e., time $t_I$) is the blood pressure in the brachial artery at the time $t_I$.

At the time $t_I$, if the width of the midstream blocking airbag is sufficient, the blood pressure in the brachial artery at the position of the midstream signal channel is approximately equal to the air pressure in the midstream blocking airbag and the following equation (1) is satisfied:

$$P_{2I} = H_{2I} \tag{1}$$

Step 2: The lateral pressure $P_{2I}$ of the blood on the brachial artery at the position of the upstream signal channel at the time $t_I$ is calculated according to the blood pressure $P_{1I}$ in the brachial artery at the position of the midstream airbag at the time $t_I$.

During the measurement, the blood flow in the brachial artery is blocked after the midstream airbag is inflated and pressurized. At this time, the blood pressure $P_{2I}$ in the brachial artery at the position of the midstream airbag satisfies the following equation (2):

$$P_{2I} = P_C - \rho a_I L_2 \tag{2}$$

In equation (2), $P_C$ is the central arterial pressure, $a_I$ is the acceleration of the blood flow at the time $t_I$, $L_2$ is the length of the blood vessel from the junction between one end of the left subclavian artery and the ascending aorta to the midstream airbag, and ρ is the density of the blood.

The sensor or inflatable airbag of the upstream signal channel only appropriately pressurizes the measured limb and feels the brachial arterial pulse wave at the position of the upstream signal channel but doesn't block the blood flow. Therefore, at the position of the upstream signal channel at the time $t_I$, the lateral pressure $P_{1I}$ of the blood in the brachial artery on the blood vessel of the brachial artery satisfies the following equation (3):

$$P_{1I} = P_C - \rho a_I L_1 - \frac{1}{2}\rho V_I^2 \tag{3}$$

In expression (3), $V_I$ is the blood flow rate in the brachial artery at the time $t_I$, and $L_1$ is the length of the blood vessel from the junction between one end of the left subclavian artery and the ascending aorta to the upstream channel.

At the time $t_I$, the blood flow rate in the brachial artery is approximately 0, i.e., $V_I \approx 0$. Moreover, in the measurement, the upstream channel is as close as possible to the midstream airbag, so it can be deemed that $L_1 \approx L_2$. Then, the following equation can be obtained according to equations (2) and (3):

$$P_{1I} = P_{2I} - \rho a(L_1 - L_2) - \frac{1}{2}\rho V_I^2 \approx P_{2I} \tag{4}$$

Then, the following equation can be obtained according to equations (1) and (4):

$$P_{1I}=H_{2I} \tag{5}$$

That is to say, the blood pressure in the brachial artery at the position of the upstream channel at the time $t_I$ is equal to the air pressure in the airbag at the time $t_I$.

Step 3: The blood pressure $P_{1II}$ in the brachial artery at the time $t_{II}$ is calculated, according to the pressure curve of the upstream channel in a pulse cycle where time $t_I$ is located in the time zone $t_x$ and the blood pressure $P_{1I}$ in the brachial artery at the position of the upstream channel at the time $t_I$.

Owing to the fact that the degree of pressurization of the upstream signal channel sensor on the brachial artery (i.e., the air pressure in the upstream airbag) is constant in the semi-blocked time zone $t_y$, the proportional relationship between the signal intensity of the air pressure in the upstream airbag and the blood pressure in the brachial artery remains unchanged in the heartbeat cycle where time $t_I$ is located.

Therefore, the following equation (6) is satisfied:

$$\frac{(P_{1II}-P_d)}{(H_{1II}-H_d)}=\frac{(P_{1I}-P_d)}{(H_{1I}-H_d)} \tag{6}$$

Then, the following equation is obtained:

$$P_{1II}=\frac{(P_{1I}-P_d)(H_{1II}-H_d)}{(H_{1I}-H_d)}+P_d \tag{7}$$

Step 4: The blood pressure $P_{1III}$ in the brachial artery at the position of the upstream signal channel at the time $t_{III}$ in the completely blocked time zone $t_x$ is calculated, according to the blood pressure $P_{1II}$ in the brachial artery at the position of the upstream signal channel at the time $t_{II}$ in the semi-blocked time zone $t_y$. According to the definition of time $t_{II}$, the acceleration a of the blood movement in the brachial artery at this moment is a=0.

At the time $t_{II}$, the blood pressure $P_{1II}$ in the brachial artery at the position of the upstream signal channel satisfies the following equation (8):

$$P_{1II}=P_{CII}-\rho aL_1-\frac{1}{2}\rho V^2=P_{CII}-\frac{1}{2}\rho V_{II}^2 \tag{8}$$

where $V_{II}$ is the blood flow rate in the brachial artery at the time $t_{II}$. The blood flow rate in the brachial artery in a normal person in a completely open state is 60-100 cm/s; suppose the blood density ρ is ρ=1 g/cm$^3$, the maximum effect of blood flow rate on pressure is as follows, according to the maximum blood flow rate $V_{max}$=100 cm/s in the brachial artery:

$$|P_{1II}-P_{CII}|=\Delta P\ll\Delta P_{max}=\frac{1}{2}\rho V_{max}^2=500\text{ Pa}=3.75\text{ mmHg}$$

Since the brachial artery is partially blocked and the blood flow rate in the brachial artery is much lower than the maximum blood flow rate in a completely open state at the time $t_{II}$, the influence of blood flow rate on pressure is much lower than 3.75 mmHg at the time $t_{II}$, and can be ignored.

Therefore:

$$P_{1II}=P_{CII}-\Delta P\approx P_{CII} \tag{9}$$

At the time $t_{III}$, since the blood flow rate and acceleration in the brachial artery are close to zero because the current time is in the completely blocked time zone $t_x$, then:

$$V_{III}\approx 0,\ a_{III}\approx 0,$$

where $V_{III}$ is the blood flow rate in the brachial artery at the time $t_{III}$, and $a_{III}$ is the blood flow acceleration at the time $t_{III}$:

$$P_{1III}=P_{CIII}-\rho a_{III}L_1-\frac{1}{2}\rho V_{III}^2\approx P_{CIII} \tag{10}$$

In short-time measurement, it can be deemed that the central arterial pressure and the rising edge of its waveform remain unchanged. That is to say, for the heartbeat cycle in which time $t_{II}$ and time $t_{III}$ are located, if the pulse upstroke time points are $t_{xC}$ and $t_{yC}$ respectively, then:

$$P_C|_{(t_{xC}+t)}=P_C|_{(t_{yC}+t)}$$

where t is any time interval smaller than a heartbeat cycle.

Therefore, since the delay time Δt of the pulse upstroke at the time $t_{II}$ is the same as the delay time Δt of the pulse upstroke at the time $t_{III}$, then the following formula (11) is satisfied:

$$P_{CII}=P_{CIII} \tag{11}$$

The following equation can be obtained from equations (9), (10) and (11):

$$P_{1III}=P_{1II} \tag{12}$$

Step 5: A maximum value $P_{1s}$ of the blood pressure in the brachial artery at the position of the upstream signal channel is calculated, according to the pressure curve of the upstream signal channel in the heartbeat cycle where time $t_{III}$ is located and the blood pressure $P_{1III}$ in the brachial artery at the position of the upstream signal channel at the time $t_{III}$ and the systolic pressure $P_{cs}$ of the central artery is obtained approximately.

Owing to the fact that the blood flow rate and acceleration in the brachial artery are close to zero in the completely blocked time zone $t_x$, and the measuring airbag is kept at the same level as the ascending aorta during the measurement, the systolic pressure of the central artery is approximately equal to the maximum value $P_{1s}$ of the blood pressure in the brachial artery at the position of the upstream signal channel, i.e., $P_{CS}\approx P_{1s}$.

Owing to the fact that the degree of pressurization of the upstream signal channel sensor on the brachial artery or the air pressure in the upstream airbag is constant in the completely blocked time zone $t_x$, the proportional relationship between the signal intensity of the air pressure in the upstream airbag and the blood pressure in the brachial artery remains unchanged in the heartbeat cycle where time $t_{III}$ is located.

$$\frac{(P_{1s}-P_d)}{(H_{1s}-H_d)}=\frac{(P_{1III}-P_d)}{(H_{1III}-H_d)} \tag{13}$$

The following equation can be obtained from the equations (5), (7), (12), and (13):

$$P_{1s}=\frac{(P_{1III}-P_d)(H_{1s}-H_d)}{(H_{1III}-H_d)}+P_d=\frac{(P_{1II}-P_d)(H_{1s}-H_d)}{(H_{1III}-H_d)}+P_d=\frac{(H_{2I}-P_d)(H_{1II}-H_d)(H_{1s}-H_d)}{(H_{1I}-H_d)(H_{1III}-H_d)}+P_d \tag{14}$$

$$P_{cs}=P_{1s} \tag{15}$$

Thus, the novel non-invasive central arterial pressure measurement method in the present invention utilizes a three-channel pulse wave signal sensor to obtain pulse wave signals, and then obtains accurate central arterial pressure and other intraluminal large arterial pressures. The method has the following features:

Feature 1: A midstream blocking airbag is used, and is inflated to a pressure much higher than the systolic pressure of arterial blood. In that state, the arterial blood vessel is completely blocked, and the blood in the blood vessel essentially doesn't flow. Thus, the influence of blood flow on the measurement of the central arterial pressure is eliminated. Therefore, the blood pressure that is felt by the midstream blocking airbag is approximately equal to the central arterial pressure.

Feature 2: A midstream blocking airbag is used, and a downstream pulse wave detector is mounted downstream of the midstream blocking airbag in the arterial blood flow direction. As the blocking airbag deflates after it is inflated and blocks the arterial blood flow, the air pressure value of the blocking airbag corresponding to the moment of an upstroke of the output signal of the downstream pulse wave detector is acquired when the blocking airbag reaches a semi-blocked state. If the width of the blocking airbag is sufficient, the air pressure value of the blocking airbag corresponding to the upstroke is approximately equal to the blood pressure in the artery at that moment.

Feature 3: An upstream pulse wave detector is mounted upstream of the blocking airbag in the arterial blood flow direction. At the moment of an upstroke of the output signal of the downstream pulse wave detector, the blood flow rate in the artery is approximately zero, and the blood pressure in the artery at the position of the upstream pulse wave detector is equal to the blood pressure in the artery at the position of the blocking airbag.

Feature 4: A second derivative of the air pressure fluctuation curve when the midstream blocking airbag reaches the semi-blocked state is calculated to find out the first zero-crossing point from positive to negative, i.e., a zero-crossing point of blood flow acceleration, and a delay time from the upstroke of the pulse wave to the zero-crossing point of acceleration is measured; for the semi-blocked state and the completely blocked state, a respective delay time point from the upstroke of the pulse wave is found out respectively for the pulse wave signal of a heartbeat cycle in each of the two states, and the pressures in the artery at the upstream pulse wave detection positions corresponding to the two time points are approximately equal to each other.

Feature 5: The tightness of the upstream pulse detector mounted on the limb remains unchanged during the measurement; or the inflation pressure remains unchanged during the measurement in the case that the upstream pulse wave detector is an inflatable airbag. Thus, the output signal intensity of the upstream pulse detector is directly proportional to the blood pressure in the blood vessel at the upstream position.

Feature 6: The signal curve of the upstream pulse wave detector in the completely blocked state and the pressure in the artery at the upstream pulse wave detection position at the moment of the zero-crossing point of acceleration are acquired, and a maximum pressure in the artery at the upstream pulse wave detection position is obtained through calculation. The maximum pressure is approximately equal to the systolic pressure of the central artery.

The widths and positions of the three signal channels of the three-channel pulse wave signal sensor will be described below.

I. Determination of the widths and positions of the upstream, midstream and downstream airbag straps 1. The width of the midstream airbag strap is determined by the circumference of the upper limb of the subject. The requirement for the correspondence relationship between the width and the circumference of the upper limb of the subject is the same as that for the cuff of a Korotkoff sound sphygmomanometer. If the circumference of the upper limb of the subject is relatively large, the width of the midstream airbag strap should be increased accordingly; if the circumference of the upper limb of the subject is relatively small, the width of the midstream airbag strap should be decreased accordingly.
2. The widths of the upstream and downstream airbag straps should not be too great or too small. If the widths of the upstream and downstream airbag straps are too small, the outputted pressure signals will be too small, and the measurement accuracy will be affected; if the widths of the upstream and downstream airbag straps are too great, the time resolution accuracy will be degraded; besides, limited by the length of the upper limb of the subject, the widths of the upstream and downstream airbag straps can't be too great.

Usually, the widths of the upstream and downstream airbag straps are within a range of 1-5 cm, preferably 2-3 cm, which is suitable for measurement accuracy and time resolution accuracy.

3. In order to ensure measurement accuracy, the upstream airbag strap should be as close as possible to the position where the limb is close to the body, and the upper edge of the midstream airbag strap should be as close as possible to the lower edge of the upstream airbag strap, but advantageously the midstream airbag strap and the upstream airbag strap are not connected together completely; otherwise mutual interference between the upstream airbag strap and the midstream airbag strap may occur.

In actual measurement, if the length of the upper limb permits, the upstream, midstream and downstream airbag straps may be placed on the upper limb above the elbow joint at the same time, or the upstream and midstream airbag straps may be placed on the upper limb above the elbow joint, while the downstream airbag strap may be placed below the elbow joint.

When the measurement is made on a lower limb, the downstream airbag strap may be bound at a position below the knee joint.

II. In the case that the upstream and/or downstream signal channels employ electronic signal sensors, such as pressure sensors or photoelectric sensors, a strap bracket may be used to fix the upstream and downstream pressure sensors or photoelectric sensors, and the midstream airbag strap. The spacings among the upstream, midstream and downstream devices and the positions of the upstream, midstream and downstream devices are determined by the strap bracket; specifically, the spacing between the center of the upstream electronic signal sensor and the upper edge of the midstream airbag may be between 0 cm and 15 cm, typically is 1 cm. The spacing between the center of the downstream electronic signal sensor and the lower edge of the midstream airbag may be between 0 cm and 30 cm, typically 1 cm.

The fixing bands for the upstream and downstream sensors are fixed on the strap bracket. In the actual measurement application, the tightness of the fixing bands for the upstream and downstream electronic signal sensors is appropriate so that the upstream and downstream electronic signal sensors are fixed stationarily on the body surface at the artery in the limb to be measured without affecting the blood flow.

Similar to sensor straps employing three airbags, the upstream electronic signal sensor of the sensor strap employing an electronic signal sensor for the upstream signal channel is as close as possible to the part of the limb close to the body, and the upper edge of the midstream airbag strap is as close as possible to the lower edge of the upstream electronic signal sensor, but advantageously the midstream airbag strap and the upstream electronic signal sensor are not connected together completely; otherwise mutual interference between the upstream signal channel and the midstream signal channel may occur.

In actual measurement, if the length of the upper limb permits, the upstream, midstream and downstream signal channels may be placed on the upper limb above the elbow joint at the same time, or the upstream and midstream signal channels may be placed on the upper limb above the elbow joint, while the downstream signal channel may be placed below the elbow joint, or even placed at the artery at the wrist.

When the measurement is made on a lower limb, the downstream electronic signal sensor may be placed at a position below the knee joint.

In the three-channel pulse wave signal sensor in the present invention, at least the midstream signal channel employs an inflatable airbag, and the inflatable airbag is fixed by means of a strap, while the upstream and midstream signal channels are not necessarily fixed by means of straps, as long as the upstream and downstream electronic signal sensors are fixed stationarily on the body surface at the artery in the limb to be measured, without affecting the blood flow. In other words, the upstream, midstream and downstream signal channels may be integral or separated; moreover, even if they are integral, their main bodies may be spaced apart from each other and connected simply via connecting structures, which may be brackets, connecting strips, or the like.

In order to attain the objects of the present invention, the present invention provides a novel non-invasive method for measuring central arterial pressure and other intraluminal large arterial pressures, which utilizes a three-channel pulse wave signal sensor to obtain pulse wave signals, wherein the three-channel pulse wave signal sensor is divided into an upstream signal channel, a midstream signal channel and a downstream signal channel according to the blood flow direction, corresponding to a measured limb; the upstream signal channel is a strap body with a built-in inflatable airbag or an upstream electronic signal sensor, the midstream signal channel is a midstream strap of the strap body with a built-in inflatable airbag, the downstream signal channel is a strap body with a built-in inflatable airbag or a downstream electronic signal sensor, and the measured limb is an upper limb or a lower limb; the method comprises the following steps: step C: inflating the airbag of the midstream strap, and acquiring and detecting pulse wave output signals of the upstream and downstream signal channels at the same time, till the blood flow in a brachial artery or femoral artery is stopped, i.e., the pulse wave output signal of the downstream signal channel is zero; logging the air pressure value of the midstream strap airbag at this time, inflating the airbag of the midstream strap further, and monitoring the air pressure of the midstream strap, till the air pressure of the midstream strap is greater than the logged air pressure value by 10-100 mmHg, then stopping the inflation; at that point, the blood flow in the brachial artery or femoral artery is completely blocked; then acquiring pulse wave output signals of the upstream channel for several heartbeat cycles; step D: controlling the airbag of the midstream strap to deflate gradually, and acquiring the output signals of the upstream, midstream and downstream signal channels via signal amplifiers synchronously at the same time; as pulse wave signals gradually appear in the downstream signal channel, indicating that the blood in the brachial artery or femoral artery gradually begins to flow, the blood flow in the brachial artery or femoral artery is in a semi-blocked state, and the output signals of the upstream, midstream and downstream signal channels are acquired in the process; and, determining the moment of an upstroke of the pulse wave signal of the downstream channel by acquiring several pulse wave signals initially appearing in the downstream signal channel, and, at the same time, measuring the air pressure in the airbag of the midstream signal channel corresponding to the moment of the upstroke to obtain the blood pressure in the brachial artery or femoral artery at the position of the midstream signal channel at the moment; owing to the fact that the blood flow rate is approximately zero at the moment of the upstroke of the pulse wave signal of the downstream channel, the blood pressure in the brachial artery or femoral artery at the position of the upstream channel is equal to the blood pressure in the brachial artery or femoral artery at the position of the midstream signal channel, thus the blood pressure in the brachial artery or femoral artery at the position of the upstream channel is equal to the air pressure in the airbag of the midstream strap at that moment; step E: in the semi-blocked state, logging the amplitudes of several pulse wave signals appearing initially in the downstream signal channel, logging the air pressure in the airbag of the midstream signal channel at each pulse synchronously, and performing linear fitting between them to calculate a corresponding air pressure in the airbag of the midstream signal channel when the amplitude of the pulse wave signal of the downstream signal channel crosses zero; that air pressure is the systolic pressure of the brachial artery or femoral artery; as the airbag of the midstream strap continues deflating, measuring a time delay between an air pressure fluctuation signal of the airbag of the midstream strap and the pulse wave signal of the downstream signal channel, and performing fitting and calculating a time point when the time delay gradually decreases to a constant value; at that time point, the pressure of the midstream airbag corresponds to the diastolic pressure of the brachial artery or femoral artery, which is used to calculate the systolic pressure of the central artery or other intraluminal aortae; step F: calculating the systolic pressure and diastolic pressure of the central artery or other intraluminal aortae, according to the pulse wave signals of the upstream and downstream signal channels, the air pressure signal of the midstream airbag and the diastolic pressure of the brachial artery or femoral artery that are acquired synchronously in the above process; now, the measurement is finished; wherein a maximum value of the blood pressure in the brachial artery or femoral artery in the completely blocked state is obtained according to the delayed time point in the completely blocked state, the blood pressure in the brachial artery or femoral artery at the position of the upstream signal channel, and a pulse wave signal curve of the upstream signal channel for several heartbeat cycles in the completely blocked state, which is acquired in step C; the maximum value of the blood pressure in the brachial artery or femoral artery in the completely blocked state is approximately equal to the systolic pressure of the central artery or other intraluminal aortae; and, near the diastolic pressure point, the blood flow rate in the brachial artery or femoral artery is approximately zero; therefore, the diastolic pressure measured at the position of the brachial artery or femoral artery is approximately equal to the diastolic pressure of central artery or other intraluminal aortae.

As a preferred embodiment, in the step D: a second derivative of the air pressure fluctuation curve of the airbag of the midstream signal channel in the semi-blocked state is calculated, and a first zero-crossing point from positive to negative, i.e., a zero-crossing point of blood flow acceleration, is found out; the blood pressure in the brachial artery or femoral artery at the position of the upstream channel at the moment of the zero-crossing point of blood flow acceleration in the semi-blocked state is calculated according to the signal curve of the upstream signal channel at this moment and the blood pressure in the brachial artery at the position of the upstream signal channel at the moment of the upstroke of the pulse wave signal of the downstream signal channel in the semi-blocked state; and a delay time between the pulse upstroke and the zero-crossing point of blood flow acceleration in the semi-blocked state is calculated for a heartbeat cycle of the pressure curve of the airbag of the midstream signal channel; a corresponding delay time point (i.e., the delay time from the pulse upstroke to this point is the same as the above-mentioned delay time) in the completely blocked state is determined for a heartbeat cycle of the signal curve of the upstream signal channel; the blood pressure in the brachial artery or femoral artery at the position of the upstream signal channel at that delay time point in the completely blocked state is approximately equal to the blood pressure in the brachial artery or femoral artery the position of the upstream signal channel at the same delay time point in the semi-blocked state.

As a preferred embodiment, in the measurement process, the airbag of the midstream strap is kept at the same level as the intraluminal large artery to be measured, wherein when the left arm is to be measured, the intraluminal large artery is the ascending aorta; when the right arm is to be measured, the intraluminal large artery is the innominate artery; when a lower limb is to be measured, the intraluminal large artery is the terminal of the abdominal aorta.

As a preferred embodiment, the inflatable airbag of the midstream strap is connected to one end of a two-way air valve through a tube, and the other end of the two-way air valve is connected to a pressure sensor, an air pump and a linear air valve through a tube, wherein, in step C, the midstream strap is inflated by opening the two-way air valve, closing the linear air valve and starting the air pump; in the step D, the midstream strap is controlled to deflate gradually by opening the two-way air valve connected to the inflatable airbag of the midstream strap and gradually opening the linear air valve.

As a preferred embodiment, both the upstream signal channel and the downstream signal channel are strap bodies with built-in inflatable airbags, and the inflatable airbag of the upstream signal channel is connected to one end of a first two-way air valve through a tube, and is connected to a first pressure sensor through a tube at the same time; the inflatable airbag of the midstream signal channel is connected to one end of a second two-way air valve through a tube, and is connected to a microporous air valve through a tube at the same time, and the microporous air valve is connected to the inflatable airbag of the downstream signal channel through a tube; the inflatable airbag of the downstream signal channel is connected to one end of a third two-way air valve through a tube, and is connected to the second pressure sensor and the microporous air valve through a tube at the same time; the other ends of the three two-way air valves are connected together through a tube and is connected to the third pressure sensor, the air pump and the linear air valve through a tube, and the first, second and third pressure sensors are respectively connected to first, second and third signal amplifiers through electric wires, wherein the method further comprises the following step B before the step C: starting the air pump to inflate the inflatable airbag of the upstream signal channel to tens of millimeters of mercury via the two-way air valve of the upstream signal channel, and synchronously acquiring pulse wave signals of the upstream and downstream signal channels and air pressure signals of the inflatable airbag of the midstream signal channel, till the measurement is finished; and the step C is: opening the two-way air valve connected to the inflatable airbag of the midstream signal channel, and gradually opening the linear air valve, so that the inflatable airbag of the midstream signal channel gradually deflates, the blood in the brachial artery or femoral artery gradually begins to flow, and pulse wave signals begin to appear in the downstream signal channel; the current state is a semi-blocked state; logging the amplitudes of several pulse wave signals appearing initially in the downstream signal channel, logging the air pressure in the inflatable airbag of the midstream signal channel at each pulse synchronously, and performing linear fitting between them to calculate a corresponding air pressure in the inflatable airbag of the midstream signal channel when the amplitude of the pulse wave signal of the downstream signal channel crosses zero; that air pressure is the systolic pressure of the brachial artery or femoral artery; as the inflatable airbag of the midstream signal channel continues deflating, measuring a time delay between the air pressure fluctuation signal of the inflatable airbag of the midstream signal channel and the pulse wave signal of the downstream signal channel, and performing fitting and calculating a time point when the time delay gradually decreases to a constant value; at that moment, the pressure of the inflatable airbag of the midstream signal channel is the diastolic pressure of the brachial artery or femoral artery.

As a preferred embodiment, the method further comprises the following step A before the step B: opening the two-way air valve connected to the inflatable airbag of the midstream signal channel, closing the linear air valve, and starting the air pump to inflate the inflatable airbag of the midstream signal channel via the two-way air valve and inflate the inflatable airbag of the downstream signal channel via the microporous air valve, and acquiring and detecting the air pressure fluctuation signal of the inflatable airbag of the downstream signal channel at the same time, till the blood flow in the brachial artery or femoral artery is stopped, i.e., the pulse wave signal of the inflatable airbag of the downstream signal channel is zero; opening the two-way air valve connected to the inflatable airbag of the midstream signal channel, and gradually opening the linear air valve, so that the inflatable airbag of the midstream signal channel gradually deflates, the blood in the brachial artery or femoral artery gradually begins to flow, and pulse wave signals begin to appear in the downstream signal channel; logging the amplitudes of several pulse wave signals initially appearing in the downstream signal channel, and logging the air pressure of the inflatable airbag of the midstream signal channel at each pulse synchronously, performing linear fitting between them, and calculating the air pressure of the inflatable airbag of the midstream signal channel corresponding to the moment when the amplitude of the pulse wave signal of the downstream signal channel crosses zero; that air pressure is the systolic pressure of the brachial artery or femoral artery; as the inflatable airbag of the midstream signal channel continues deflating, measuring a time delay between the air pressure fluctuation signal of the inflatable airbag of the midstream signal channel and the pulse wave signal of the downstream signal channel, and performing fitting and calculating a time point when the time delay gradually decreases to a constant value; at that moment, the pressure of the inflatable airbag of the midstream signal channel is the diastolic pressure of the brachial artery or femoral artery; and "inflating the inflatable airbag of the upstream signal channel via the two-way valve of the upstream signal channel to tens of millimeters of mercury" in the step B means "inflating the inflatable airbag of the upstream signal channel via the two-way valve of the upstream signal channel to the diastolic pressure of the brachial artery or femoral artery obtained in the step A".

In another aspect, the present invention further provides a three-channel pulse wave signal sensor, which is divided into an upstream signal channel, a midstream signal channel and a downstream signal channel in a blood flow direction, corresponding to a measured limb; the upstream signal channel, the midstream signal channel and the downstream signal channel are respectively fixed at the upstream, the midstream and the downstream in the blood flow direction during blood pressure measurement, the upstream signal channel is a strap body with a built-in inflatable airbag or an upstream electronic signal sensor, the midstream signal channel is a midstream strap in the strap body with a built-in inflatable airbag, and the downstream signal channel is a strap body with a built-in inflatable airbag or a downstream electronic signal sensor; wherein the built-in inflatable airbag of the upstream signal channel, the built-in inflatable airbag of the midstream signal channel and the built-in inflatable airbag of the downstream signal channel are respectively connected to three corresponding connecting jacks on a main unit of a non-invasive device for measuring blood pressure through air ducts, and the upstream electronic signal sensor and the downstream electronic signal sensor respectively transmit upstream and downstream pulse wave signals of blood flow to the main unit of the non-invasive device for measuring blood pressure.

As a preferred embodiment, spacings among the upstream signal channel, the midstream signal channel and the downstream signal channel are designed according to the length of the measured limb, and the three signal channels can be closely connected into an integral structure or spaced from each other by means of a connecting structure.

As a preferred embodiment, the spacing between an edge of the upstream signal channel and an edge of the midstream signal channel is within a range of 0 cm to 15 cm, typically is 1 cm; the spacing between an edge of the midstream signal channel and an edge of the downstream signal channel is within a range of 0 cm to 30 cm, typically 1 cm.

As a preferred embodiment, the width of the inflatable airbag of the midstream strap is determined by the circumference of the upper limb of the subject, and there is a correspondence relationship between the width and the circumference of the upper limb of the subject based on a requirement for the cuff of a Korotkoff sound sphygmomanometer, and a minimum width is determined according to the circumference of upper limb of the subject; and both the width of the inflatable airbag of the upstream signal channel and the width of the inflatable airbag of the downstream signal channel are within a range of 2-3 cm.

As a preferred embodiment, when the measurement is made on an upper limb, the inflatable airbag of the downstream signal channel can be bound at a position below the elbow joint; and, when the measurement is made on a lower limb, the inflatable airbag of the downstream signal channel can be bound at a position below the knee joint.

As a preferred embodiment, the upstream signal channel, the midstream signal channel and the downstream signal channel should be bound on the same limb to be measured, and their relative positions should be kept unchanged during use.

As a preferred embodiment, in the case that at least one of the upstream signal channel and the downstream signal channel is an electronic signal sensor, the electronic signal sensor is a pressure sensor or a photoelectric sensor.

As a preferred embodiment, in the case that all the upstream signal channel, the midstream signal channel and the downstream signal channel are strap bodies with built-in inflatable airbags, the strap body of the upstream signal channel is fixedly connected to the strap body of the midstream signal channel, the strap body of the midstream signal channel is fixedly connected to the strap body of the downstream signal channel, and the strap bodies of the upstream signal channel, the midstream signal channel and the downstream signal channel are fixedly mounted as a single strap body.

As a preferred embodiment, in the case that at least one of the upstream signal channel and the downstream signal channel is an electronic signal sensor, the electronic signal sensors of the upstream signal channel and/or the downstream signal channel and the midstream strap are fixed by means of a strap bracket, which is provided with fixing bands for fixing the electronic signal sensors of the upstream signal channel and/or the downstream signal channel, and the spacings among the upstream, midstream and downstream signal channels and the positions of the upstream, midstream and downstream signal channels are determined by the strap bracket.

As a preferred embodiment, in the case that at least one of the upstream signal channel and the downstream signal channel is an electronic signal sensor, the electronic signal sensor is also attached to the measured limb via a strap body, and the strap body of the electronic signal sensor is connected to the strap body of the midstream strap.

As a preferred embodiment, in the case that at least one of the upstream signal channel and the downstream signal channel is an electronic signal sensor, the electronic signal sensor is separated from the midstream strap.

In yet another aspect, the present invention provides a novel non-invasive device for measuring central arterial pressure and other intraluminal aortic pressures, which comprises the three-channel pulse wave signal sensor described above.

As a preferred embodiment, the novel non-invasive device for measuring central arterial pressure and other intraluminal aortic pressures further comprises a main unit, which comprises a microprocessor, wherein all the upstream signal channel, the midstream signal channel and the downstream signal channel of the three-channel pulse wave signal sensor are strap bodies with built-in inflatable airbags; the airbag of the upstream signal channel is connected to one end of a first two-way air valve through a tube, and is connected to a first pressure sensor through a tube at the same time; the airbag of the midstream signal channel is connected to one end of a second two-way air valve through a tube, and is connected to one end of a microporous air valve through a tube at the same time, and the other end of the microporous air valve is connected to the airbag of the downstream signal channel through a tube; the airbag of the downstream signal channel is connected to a third two-way air valve through a tube, and is connected to a third pressure sensor and the other end of the microporous air valve through a tube at the same time; the other ends of the first, second and third two-way air valves are connected together through tubes, and are connected to the second pressure sensor, the air pump and the linear air valve through tubes; the first, second and third pressure sensors are respectively connected to first, second and third signal amplifiers through electric wires, and output terminals of the first, second and third signal amplifiers are connected to input terminals of three analog-to-digital converters (ADCs) of the microprocessor through electric wires; and the microprocessor is connected to the first, second and third two-way air valves, the first, second and third signal pressure sensors, the linear air valve and the air pump through electric wires.

As a preferred embodiment, the novel non-invasive device for measuring central arterial pressure and other intraluminal aortic pressures further comprises a main unit, which comprises a microprocessor, wherein the upstream signal channel of the three-channel pulse wave signal sensor is an upstream electronic signal sensor, and the downstream signal channel is a downstream electronic signal sensor; the upstream electronic signal sensor is connected to a first signal amplifier through electric wires; the airbag of the midstream signal channel is connected to one end of a two-way air valve through a tube, and the other end of the two-way air valve is connected to a pressure sensor, an air pump and a linear air valve through a tube, and the pressure sensor is connected to a second signal amplifier through electric wires; the downstream electronic signal sensor is connected to a third signal amplifier through electric wires; output terminals of the first, second and third signal amplifiers are connected to input terminals of three analog-to-digital converters (ADCs) of the microprocessor through electric wires; and the microprocessor is connected to the two-way air valves, the signal pressure sensors, the linear air valve and the air pump through electric wires.

Blood flow and vascular elasticity are the main factors affecting the acquisition of pulse waveforms. In the present invention, to measure an intraluminal large arterial pressure waveform, the midstream airbag of the three-channel signal sensor may be placed at the same level as the ascending aorta in a human body; for example, the three-channel signal sensor may be fixed on the upper part of the left arm. At that point, the upstream signal channel is close to the trunk of the human body and is very close to an intraluminal large artery, such as the ascending aorta, so as to minimize the effect resulting from vascular elasticity. A maximum value of the blood pressure in the blood vessel in a completely blocked state is obtained by using the relationship between the pressure in the blood vessel and the pressure of the airbag outside the blood vessel under the condition that the width of the midstream airbag strap is sufficient, the relationship between the blood pressure in the upstream blood vessel and the blood pressure in the midstream blood vessel under the condition that the blood flow rate is zero at the moment of a pulse upstroke, and the relationship between the blood pressure in the blood vessel in the completely blocked state and the blood pressure in the blood vessel in a semi-active state under the condition that the blood flow acceleration is zero, and the maximum value is approximately equal to the systolic pressure of the intraluminal large artery. At that point, since the blood flow is in a completely blocked state, the error resulting from blood flow in the measurement is avoided to the greatest extent. Owing to the fact that the blood flow rate is close to zero at diastolic pressure, the diastolic pressure of the intraluminal large artery is approximately equal to the diastolic pressure of the brachial artery or femoral artery.

Compared with the prior art, the method and device in the present invention can achieve accurate measurement of central arterial pressure and other intraluminal large arterial pressures.

DETAILED DESCRIPTION OF THE EMBODIMENTS

Some embodiments of the novel method and device for non-invasive detection of central arterial pressure and other intraluminal large arterial pressures and the three-channel pulse wave signal sensor in the present invention will be described below with reference to the accompanying drawings.

The embodiments described herein are specific embodiments of the present invention and are intended to explain the ideal of the present invention. All these embodiments are explanatory and exemplary and shall not be interpreted as constituting any limitation to the embodiments and the scope of the present invention. Besides the embodiments described herein, those skilled in the art can use other obvious technical schemes on the basis of the disclosure in the attached claims and the specification, and these technical schemes include technical schemes that are obtained by making obvious substitutions and modifications to the embodiments described herein.

The accompanying drawings are schematic diagrams, which are provided for the purpose of aiding the explanation of the ideal of the present invention and schematically illustrate the shapes of the parts and the relationships among the parts. It should be noted that the accompanying drawings may not be drawn at the same scale for the purpose of clearly presenting the structures of the components in the embodiments of the present invention. Throughout the accompanying drawings, similar symbols represent similar elements. In addition, in the description made with reference to the accompanying drawings, terms that denote directions or orientations, such as “top”, “bottom”, “front”, and “rear”, etc., are used for the convenience of expression, but they don’t constitute any particular limitation to the structures of the features.

Embodiment 1

Figure 1:
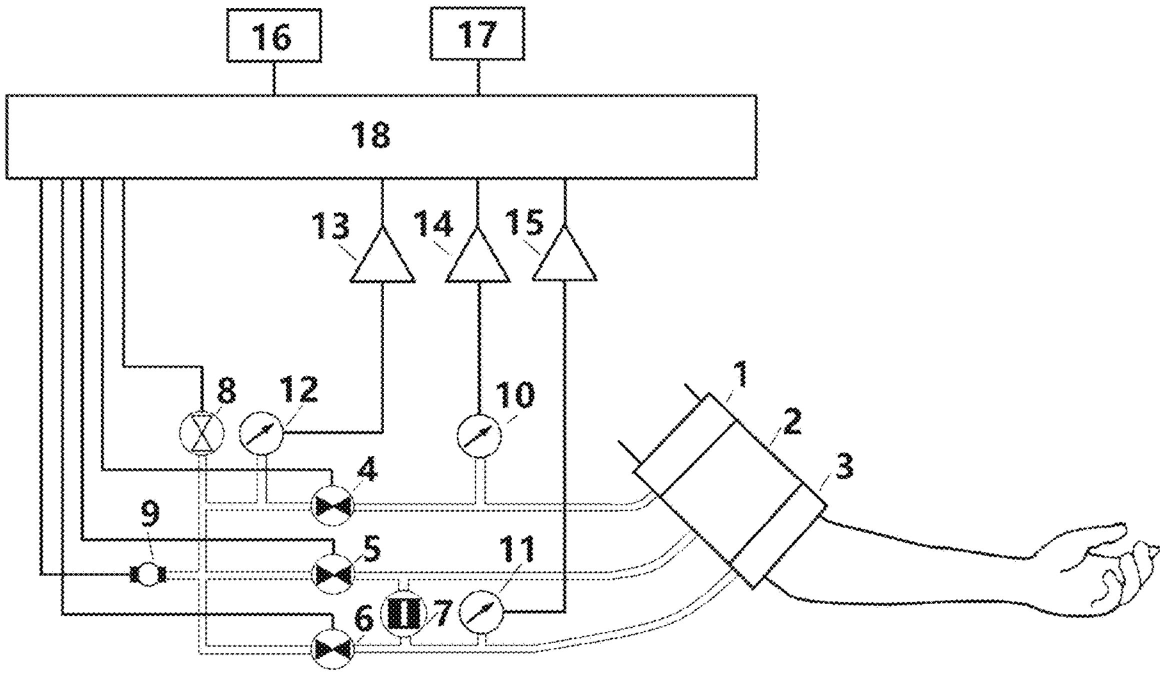
FIG. 1 is a system block diagram of a central arterial pressure measuring device using a three-channel pulse wave signal sensor.

As shown in FIG. 1, the novel non-invasive device for detection of central arterial pressure in the present invention comprises: an upstream airbag strap 1, a midstream airbag strap 2 and a downstream airbag strap 3 in a three-channel pulse wave signal sensor; two-way air valves 4, 5 and 6; a microporous air valve 7; a linear air valve 8; an air pump 9; pressure sensors 10, 11 and 12; signal amplifiers 13, 14 and 15; a display unit 16; a keyboard 17; and a microprocessor 18, etc. In the present invention, the microprocessor 18 is connected to pulse wave signal analog-to-digital converters (ADCs), or pulse wave signal ADCs are directly integrated in the microprocessor 18. A main unit of the novel non-invasive device for detection of central arterial pressure in the present invention comprises the aforementioned two-way air valves 4, 5 and 6; the microporous air valve 7; the linear air valve 8; the air pump 9; the pressure sensors 10, 11 and 12; the signal amplifiers 13, 14 and 15; and the microprocessor 18.

Figure 5:
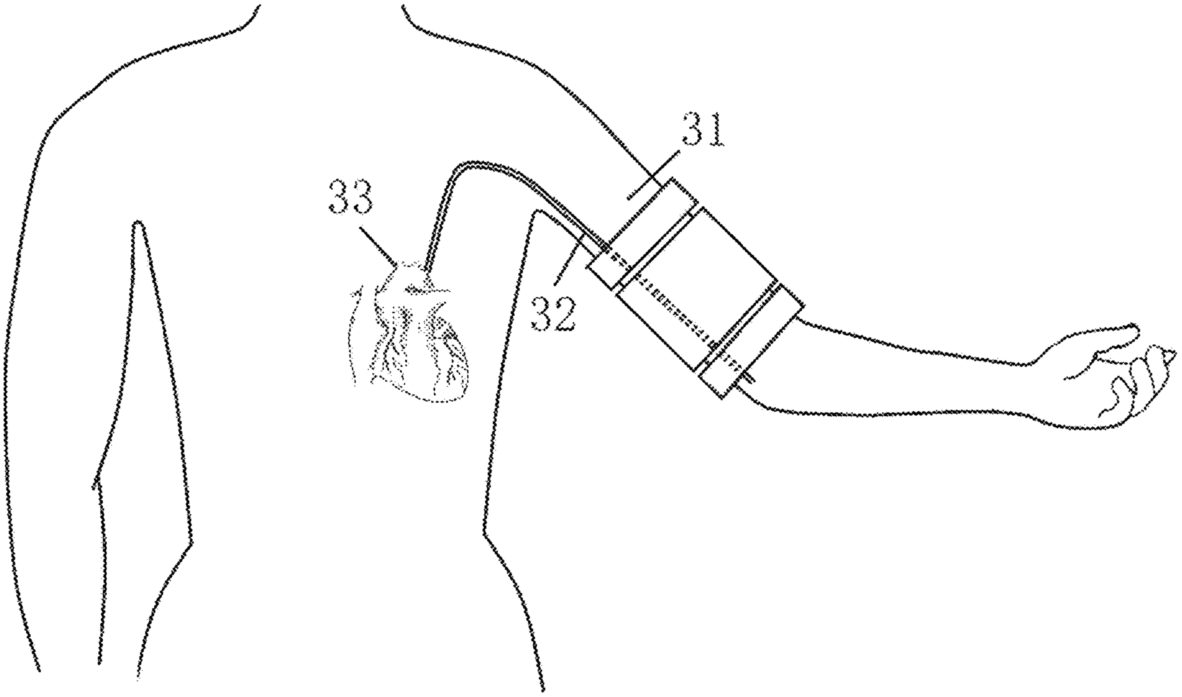
FIG. 5 is a schematic diagram of the central arterial pressure measuring device.
Figure 6:
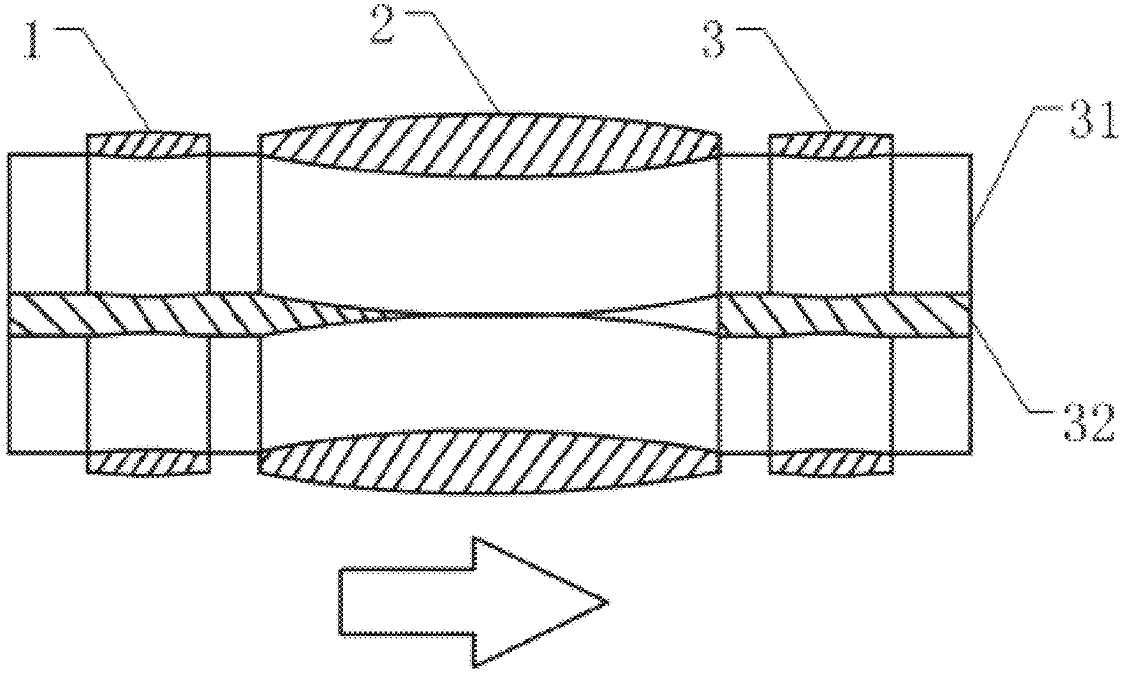
FIG. 6 is a schematic diagram of blocking the blood flow in a brachial artery with a three-airbag strap.
Figure 7:
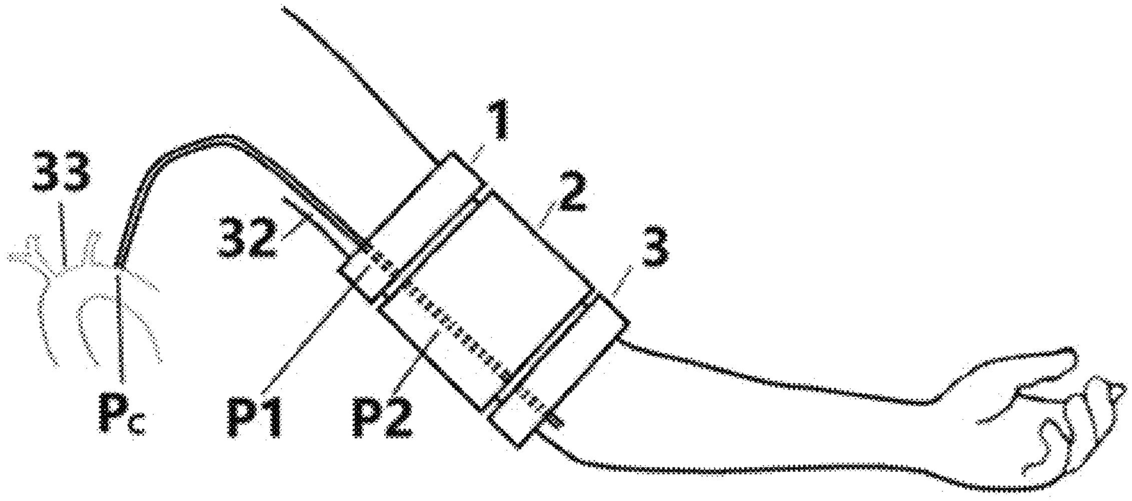
FIG. 7 is a schematic diagram of pressure analysis at various points during the measurement.

In this embodiment, the central arterial pressure is measured, for example, on an upper limb, as shown in FIGS. 1, 5, 6 and 7. In FIG. 5, the three-channel pulse wave signal sensor is fixed on an upper limb 31, and the lateral pressure of the ascending aorta 33, i.e., the central arterial pressure, is measured by measuring the pulse wave signals of a brachial artery 32. In FIG. 6, the airbag of the midstream airbag strap 2 of the three-channel pulse wave signal sensor presses the brachial artery 32 to stop the blood flow, and the brachial artery 32 is in a blocked state. In FIG. 7, $P_C$ is the central arterial blood pressure, $P_1$ is the blood pressure in the brachial artery at the position of the upstream signal channel, and $P_2$ is the blood pressure in the brachial artery at the position of the midstream airbag.

Figure 2:
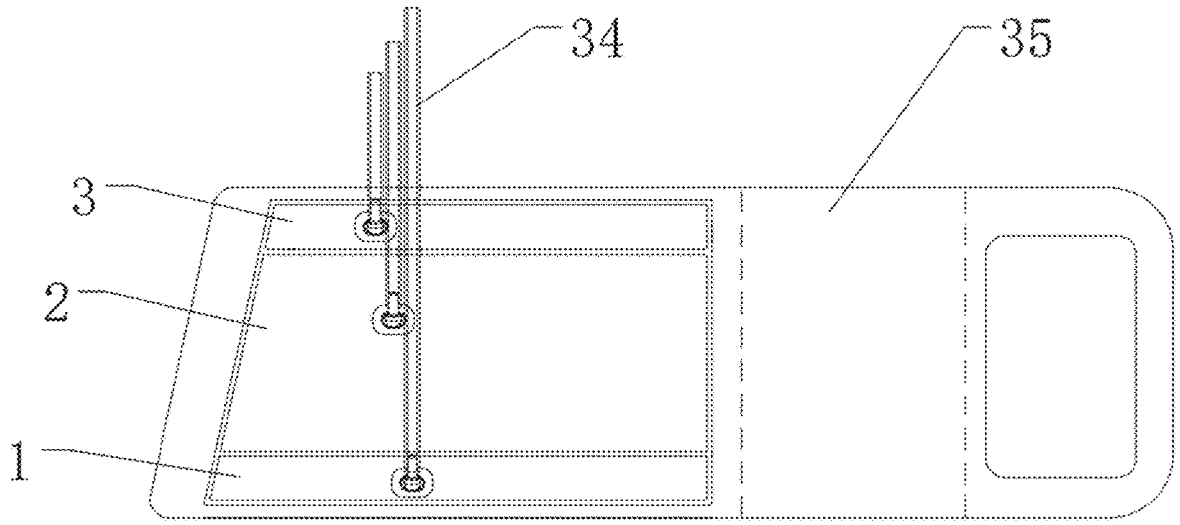
FIG. 2 is a schematic structural diagram of the first type of three-channel pulse wave signal sensor in which airbag straps are used for the upstream and downstream signal channels.
Figure 3:
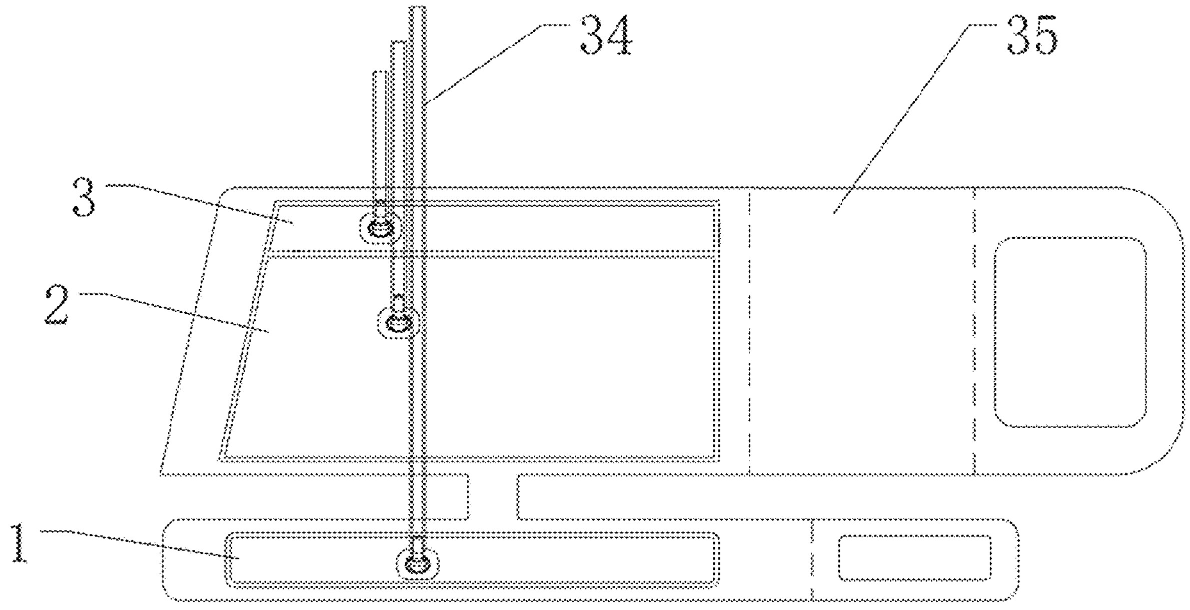
FIG. 3 is a schematic structural diagram of a second type of three-channel pulse wave signal sensor in which airbag straps are used for the upstream and downstream signal channels.
Figure 4:
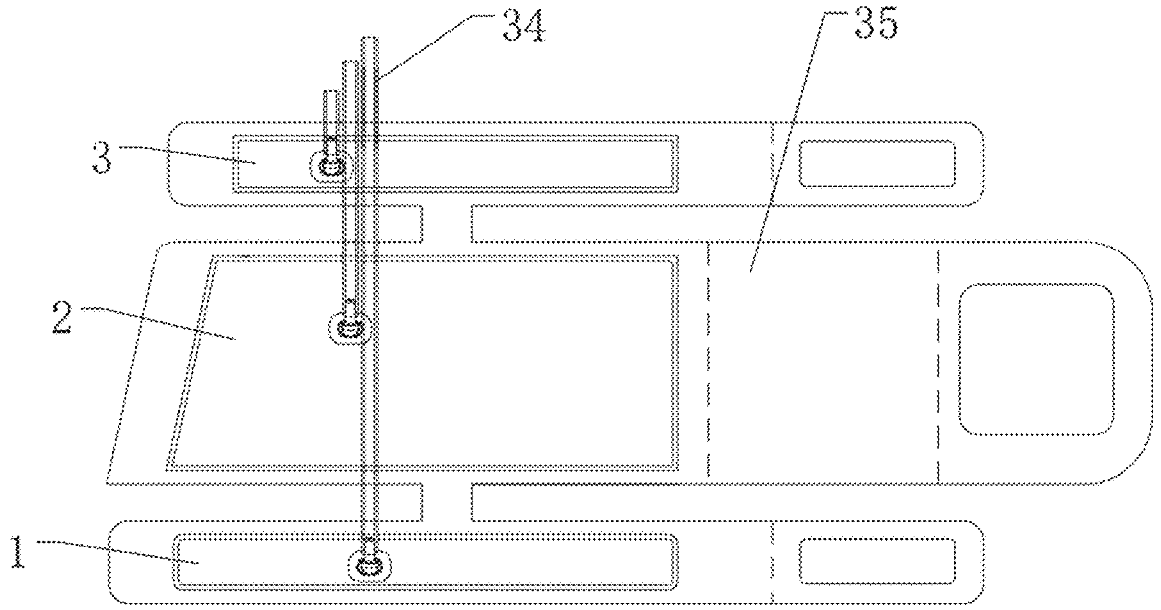
FIG. 4 is a schematic structural diagram of a third type of three-channel pulse wave signal sensor in which airbag straps are used for the upstream and downstream signal channels.

As shown in FIGS. 2-4, the three-channel pulse wave signal sensor is divided into three signal channels, namely, an upstream airbag strap 1, a midstream airbag strap 2 and a downstream airbag strap 3, in the blood flow direction. During the measurement, the midstream airbag strap 2 can block the arterial blood flow when it is inflated. The width of the airbag of the midstream airbag strap 2 is the same as the width of the airbag used in the traditional Korotkoff sound method and is determined by the circumference of the upper limb of the subject, and a minimum width is determined according to the circumference of the limb of the subject. The requirement for the correspondence relationship between the width and the circumference of the upper limb of the subject is the same as that for the cuff of a Korotkoff sound sphygmomanometer. If the circumference of the upper limb of the subject is relatively large, the width of the midstream airbag strap 2 should be increased accordingly; if the circumference of the upper limb of the subject is relatively small, the width of the midstream airbag strap 2 should be decreased accordingly. The width of the midstream airbag strap 2 may be generally classified into large size, medium size and small size, and the midstream airbag strap 2 must be available in at least two sizes.

According to the length of the measured limb of the subject, the spacings among the airbag straps of the three signal channels, namely, the upstream airbag strap 1, the midstream airbag strap 2 and the downstream airbag strap 3, may be classified into three sizes, for example, a large size, a medium size and a small size. The three signal channels may be closely connected into an integral structure or spaced by certain distances, according to the specific requirement of use. As shown in FIGS. 2, 3 and 4, the spacing between the upstream airbag strap 1 and the midstream airbag strap 2 may be between 0 cm and 15 cm, and the spacing between the midstream airbag strap 2 and the downstream airbag strap 3 may be between 0 cm and 30 cm.

The upstream airbag strap 1 is connected to the two-way air valve 4 through a tube, and is connected to the pressure sensor 10 through a tube at the same time.

The midstream airbag strap 2 is connected to the two-way air valve 5 through a tube, and is connected to the microporous air valve 7 through a tube at the same time, and the other end of the microporous air valve 7 is connected to the downstream airbag strap 3 through a tube.

The downstream airbag strap 3 is connected to the two-way air valve 6 through a tube, and is connected to the pressure sensor 11 and the other end of the microporous air valve 7 through a tube at the same time.

The other ends of the three two-way air valves 4, 5 and 6 are connected together through tubes, and are connected to the pressure sensor 12, the air pump 9 and the linear air valve 8 through tubes.

The three pressure sensors, 10, 11 and 12, are respectively connected to the signal amplifiers 14, 15 and 13 through electric wires, and the output terminals of the signal amplifiers 14, 15 and 13 are connected to the input terminals of three analog-digital converters (ADCs) of the microprocessor 18 through electric wires. Through calibration with a standard pressure gauge and computation with the microprocessor, the actual pressure values of the upstream, midstream and downstream airbag straps 1, 2 and 3 can be obtained from the signals outputted by the three pressure sensors 10, 11 and 12.

The microprocessor 18 is connected to the display unit 16 and the keyboard 17, and is connected to the three two-way air valves 4, 5 and 6, the three pressure sensors 10, 11 and 12, the linear air valve 8 and the air pump 9 through electric wires at the same time.

The built-in inflatable airbag of the upstream signal channel, the built-in inflatable airbag of the midstream signal channel and the built-in inflatable airbag of the downstream signal channel are respectively connected to three corresponding connecting jacks on the main unit of the novel non-invasive device for detection of central arterial pressure through air ducts 34.

The measurement process is as follows:

Step 1: Open the two-way air valve 5, close the two-way air valves 4 and 6, close the linear air valve 8, and start the air pump 9 to inflate the midstream airbag strap 2; at the same time, acquire and detect the output signal of the pressure sensor 11 connected to the downstream airbag strap 3, till the blood flow in the brachial artery 32 is stopped, i.e., the pulse wave signal outputted by the pressure sensor 11 is zero, and then stop the air pump 9. Gradually open the linear air valve 8, so that the midstream airbag strap 2 gradually deflates, then acquire and detect the output signal of the pressure sensor 11 connected to the downstream airbag strap 3; pulse wave signals gradually appear, indicating that the blood in the brachial artery begins to flow gradually from the blocked state. In that process, acquire the output signals of the pressure sensors 12 and 11, so as to obtain the air pressure value of the midstream airbag strap 2 and the amplitudes of the pulse wave signals of the downstream airbag strap 3. Perform linear fitting between the amplitudes of several pulse wave signals initially appearing in the downstream airbag strap 3 and the air pressure of the midstream airbag strap 2 at corresponding pulses, and calculate the air pressure of the midstream airbag strap 2 corresponding to a moment when the amplitude of the pulse wave signal of the downstream signal channel is zero; that air pressure is the systolic pressure of the brachial artery. Gradually open the linear air valve 8 further, so that the midstream airbag strap 2 continues deflating; in that process, acquire the output signals of the pressure sensors 12 and 11 to obtain an air pressure change curve of the midstream airbag strap 2 and a pulse wave signal curve of the downstream airbag strap 3; measure a time delay between the upstrokes in the above two curves, and find out an inflection point at which the time delay gradually decreases to a constant value; the pressure at that point is the diastolic pressure of the brachial artery.

Step 2: Open the two-way air valves 4, 5 and 6, and open the linear air valve 8, so that the airbag straps 1, 2 and 3 of the three channels deflate to the ambient pressure. Close the two-way air valves 5 and 6, open the two-way air valve 4, and start the air pump 9 to inflate the upstream airbag strap 1; at the same time, acquire the output signal of the pressure sensor 10 to measure the air pressure of the upstream airbag strap 1. Pressurize the upstream airbag strap 1 to about the diastolic pressure of the brachial artery according to the diastolic pressure of the brachial artery measured in step 3, then close the two-way air valve 4 and stop the air pump 9. From now on, acquire the output signals of the pressure sensors 10, 12 and 11 synchronously, till the measurement is finished.

Step 3: Close the two-way air valves 4 and 6, open the two-way air valve 5, and start the air pump 9 to inflate the midstream airbag strap 2 via the two-way air valve 5, and inflate the downstream airbag strap 3 via the microporous air valve 7 at the same time; in that process, acquire the output signal of the pressure sensor 12 at the same time to monitor the air pressure of the midstream airbag strap 2, till the air pressure of the midstream airbag strap 2 is greater than the systolic pressure of the brachial artery measured in step 2 by tens of millimeters of mercury, for example, by 10-100 mmHg typically. Stop the air pump 9 to stop the inflation of the midstream airbag strap 2.

Step 4: Stop the air pump 9 and wait for several heartbeat cycles.

Step 5: Gradually open the linear air valve 8, so that the midstream airbag strap 2 gradually deflates, then acquire and detect the output signal of the pressure sensor 11 connected to the downstream airbag strap 3; pulse wave signals gradually appear, indicating that the blood in the brachial artery begins to flow gradually from the blocked state. In that process, acquire the output signals of the pressure sensors 12 and 11, so as to obtain the air pressure value of the midstream airbag strap 2 and the amplitudes of the pulse wave signals of the downstream airbag strap 3. Perform linear fitting between the amplitudes of several pulse wave signals initially appearing in the downstream airbag strap 3 and the air pressure of the midstream airbag strap 2 at corresponding pulses, and calculate the air pressure of the midstream airbag strap 2 corresponding to a moment when the amplitude of the pulse wave signal of the downstream signal channel is zero; that air pressure is the systolic pressure of the brachial artery. Gradually open the linear air valve 8 further, so that the midstream airbag strap 2 continues deflating; in that process, acquire the output signals of the pressure sensors 12 and 11 to obtain an air pressure change curve of the midstream airbag strap 2 and a pulse wave signal curve of the downstream airbag strap 3; measure a time delay between the upstrokes in the above two curves, and find out an inflection point at which the time delay gradually decreases to a constant value; the pressure at that point is the diastolic pressure of the brachial artery. The diastolic pressure of the brachial artery is used to calculate the systolic pressure of the central artery.

Step 6: Acquire the output signals of the pressure sensors 10, 12 and 11 at different moments according to the above method, which represents the pressure data of the airbag straps 1, 2 and 3 of the upstream, midstream and downstream channels at different moments.

The method for calculating the central arterial pressure will be explained below with reference to the accompanying drawings.

Figure 8:
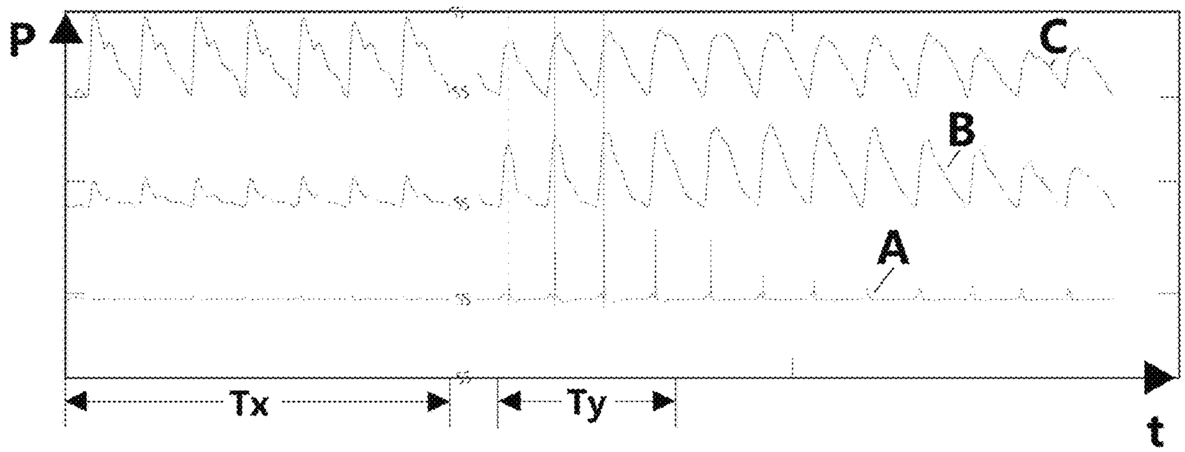
FIG. 8 shows the pressure curves of upstream, midstream and downstream airbag straps in the entire measurement process.
Figure 9:
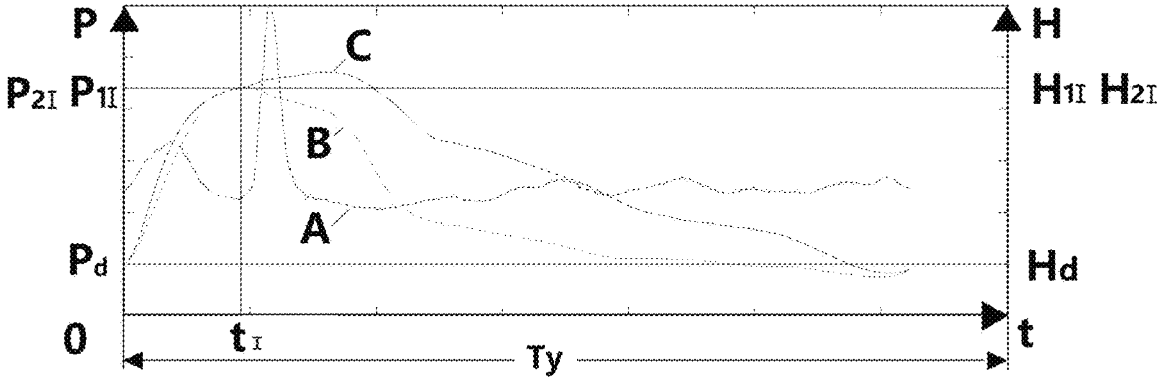
FIG. 9 shows the pressure curves of upstream, midstream and downstream airbag straps at the time $t_I$ in the semi-blocked time zone $t_y$.
Figure 10:
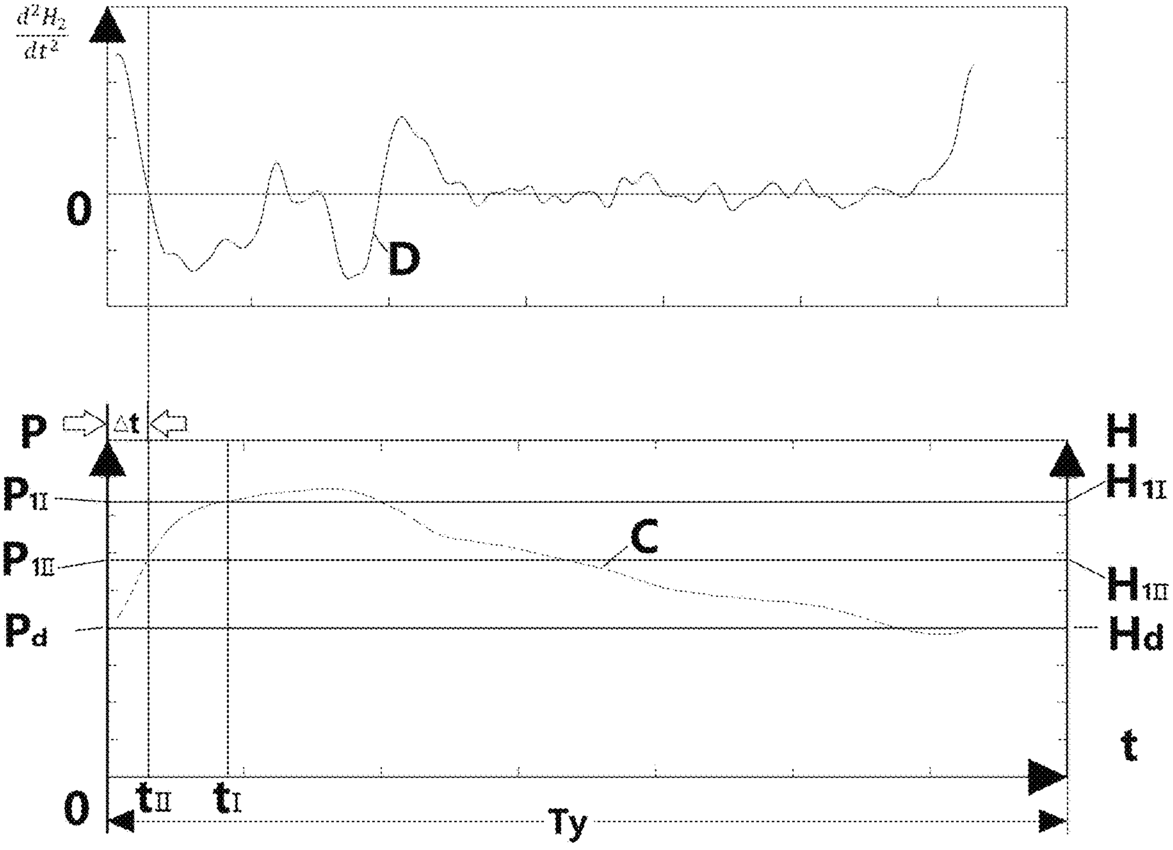
FIG. 10 shows the air pressure curve of the midstream airbag strap at the time $t_{II}$ in the semi-blocked time zone $t_y$ and the second derivative curve of air pressure.
Figure 11:
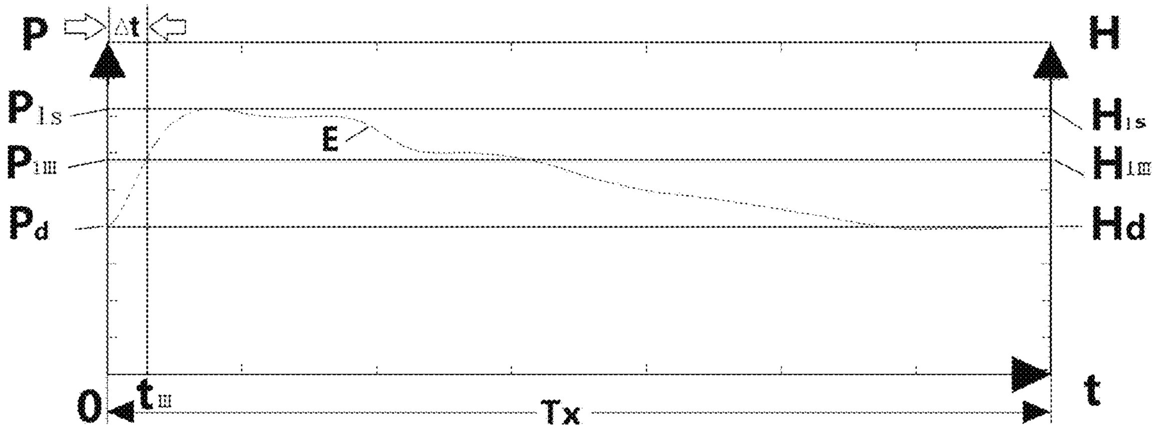
FIG. 11 shows the air pressure curve of the upstream airbag strap at the time $t_{III}$ in the completely blocked time zone $t_x$.

FIG. 8 shows the air pressure curves of the upstream, midstream and downstream airbag straps 1, 2 and 3 in the entire measurement process, wherein $t_x$ is referred to as a completely blocked time zone, in which the inflation pressure of the midstream airbag strap 2 is much greater than the systolic pressure of the brachial artery, and the blood flow in the brachial artery is completely blocked; $t_y$ is referred to as a semi-blocked time zone, in which the midstream airbag strap 2 gradually deflates after it is inflated and blocks the blood flow in the brachial artery, till the downstream signal sensor 11 begins to generate several blood flow signals. FIG. 9 shows the pressure curves of the upstream, midstream and downstream airbag straps at the time $t_I$ in the semi-blocked time zone $t_y$. FIG. 10 shows the air pressure curve of the midstream airbag strap at the time $t_{II}$ in the semi-blocked time zone $t_y$ and the second derivative curve of air pressure. FIG. 11 shows the air pressure curve of the upstream airbag strap at the time $t_{III}$ in the completely blocked time zone $t_x$.

In FIGS. 8-11, A is the air pressure curve of the downstream airbag strap 3, B is the air pressure curve of the midstream airbag strap 2, C is the air pressure curve of the upstream airbag strap 1 in the semi-blocked time zone $t_y$, and D is the blood flow acceleration curve obtained by calculating a second derivative of the air pressure curve B of the midstream airbag strap 2. E is the air pressure curve of the upstream airbag strap 1 in the completely blocked time zone $t_x$.

The specific calculation steps are as follows:

Step 1: As shown in FIG. 9, an upstroke time $t_I$ of the air pressure curve A of the downstream airbag strap 3 in a heartbeat cycle in the semi-blocked time zone $t_y$ is found out through measurement, and the blood pressure $P_{2I}$ in the brachial artery at the time $t_I$ is obtained according to the air pressure $H_{2I}$ in the midstream blocking airbag at the time $t_I$.

$$P_{2I} = H_{2I} \tag{1}$$

Step 2: The lateral pressure $P_{1I}$ of the blood on the brachial artery at the position of the upstream signal channel at the time $t_I$ is calculated according to the blood pressure $P_{2I}$ in the brachial artery at the position of the midstream airbag at the time $t_I$.

$$P_{1I} = H_{2I} \tag{5}$$

Step 3: As shown in FIG. 10, a second derivative is calculated according to the air pressure curve B of the midstream airbag strap 2 to obtain a blood flow acceleration curve D, a first zero-crossing point from positive to negative in the acceleration curve is found out, and a time $t_{II}$ is determined. The blood pressure $P_{1II}$ in the brachial artery at the time $t_{II}$ is calculated, according to the pressure curve at the position of the upstream channel at the time $t_I$ and the blood pressure $P_{1I}$ in the brachial artery at the position of the upstream channel at the time $t_I$.

$$P_{1II} = \frac{(P_{1I} - P_d)(H_{1II} - H_d)}{(H_{1I} - H_d)} + P_d \tag{7}$$

Step 4: As shown in FIG. 11, a time duration Δt from the pulse upstroke to the time $t_{II}$ in a pulse cycle in the semi-blocked time zone $t_y$ is measured, and a time $t_{III}$ in a pulse cycle in the completely blocked time zone $t_x$ is determined by delaying from the pulse upstroke by the same time duration Δt. The blood pressure P_1III in the brachial artery at the position of the upstream signal channel at the time $t_{III}$ in the completely blocked time zone $t_x$ is calculated, according to the blood pressure $P_{1II}$ in the brachial artery at the position of the upstream signal channel at the time $t_{II}$ in the semi-blocked time zone $t_y$.

$$P_{1III} = P_{1II} \tag{12}$$

Step 5: A maximum value $P_{1s}$ of the blood pressure in the brachial artery at the position of the upstream signal channel is calculated according to the pressure curve E of the upstream signal channel position at the $t_{III}$ and the blood pressure $P_{1III}$ in the brachial artery at the position of the upstream signal channel at the time $t_{III}$, so that the systolic pressure of the central artery is approximately obtained.

$$P_{1s} = \frac{(H_{2I} - P_d)(H_{1II} - H_d)(H_{1s} - H_d)}{(H_{1I} - H_d)(H_{1III} - H_d)} + P_d \tag{14}$$

$$P_{cs} = P_{1s} \tag{15}$$

Embodiment 2

Figure 12:
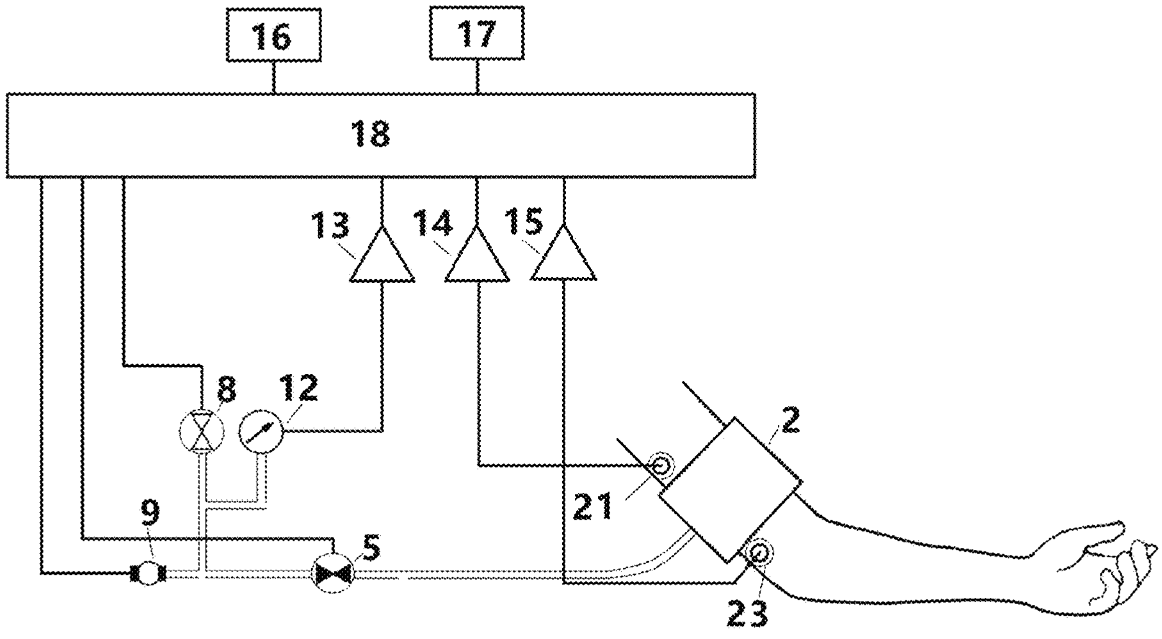
FIG. 12 is a system block diagram of a central arterial pressure measuring device in which pressure sensors or photoelectric sensors are used for the upstream and downstream signal channels, and an airbag strap is used for the midstream signal channel.

Compared with the Embodiment 1, in the Embodiment 2, one or both of the upstream and downstream airbag straps in the Embodiment 1 are replaced with electronic signal sensors. As an example, in this embodiment, the upstream and downstream airbag straps are replaced with pressure sensors or photoelectric sensors at the same time. As shown in FIG. 12, the novel non-invasive device for the detection of central arterial pressure in the present invention comprises: an upstream electronic signal sensor 21; a midstream airbag strap 2; a downstream electronic signal sensor 23; a two-way air valve 5; a linear air valve 8; an air pump 9; a pressure sensor 12; signal amplifiers 13, 14 and 15; a display unit 16; a keyboard 17; and a microprocessor 18, etc. In the present invention, the microprocessor 18 is connected to pulse wave signal analog-to-digital converters (ADCs), or pulse wave signal ADCs are directly integrated in the microprocessor 18. A main unit of the novel non-invasive device for the detection of central arterial pressure in the present invention comprises the aforementioned two-way air valves 4, 5 and 6; the linear air valve 8; the air pump 9; the pressure sensors 10, 11 and 12; the signal amplifiers 13, 14 and 15; and the microprocessor 18.

Figure 13:
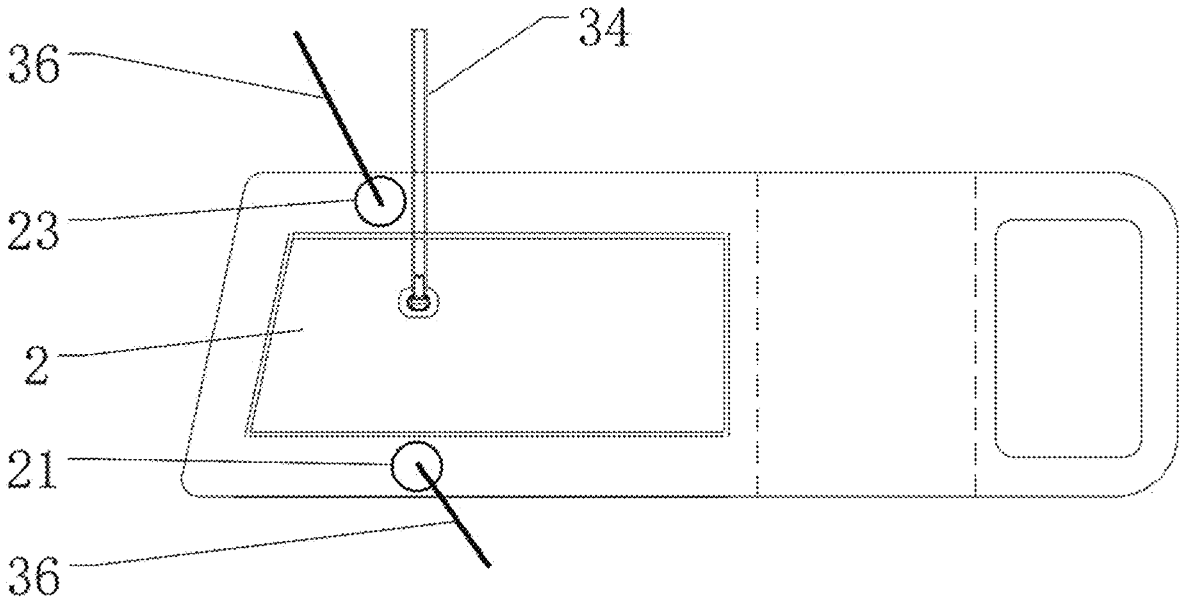
FIG. 13 is a schematic structural diagram of the first type of three-channel pulse wave signal sensor in which pressure sensors or photoelectric sensors are used for the upstream and downstream signal channels.
Figure 14:
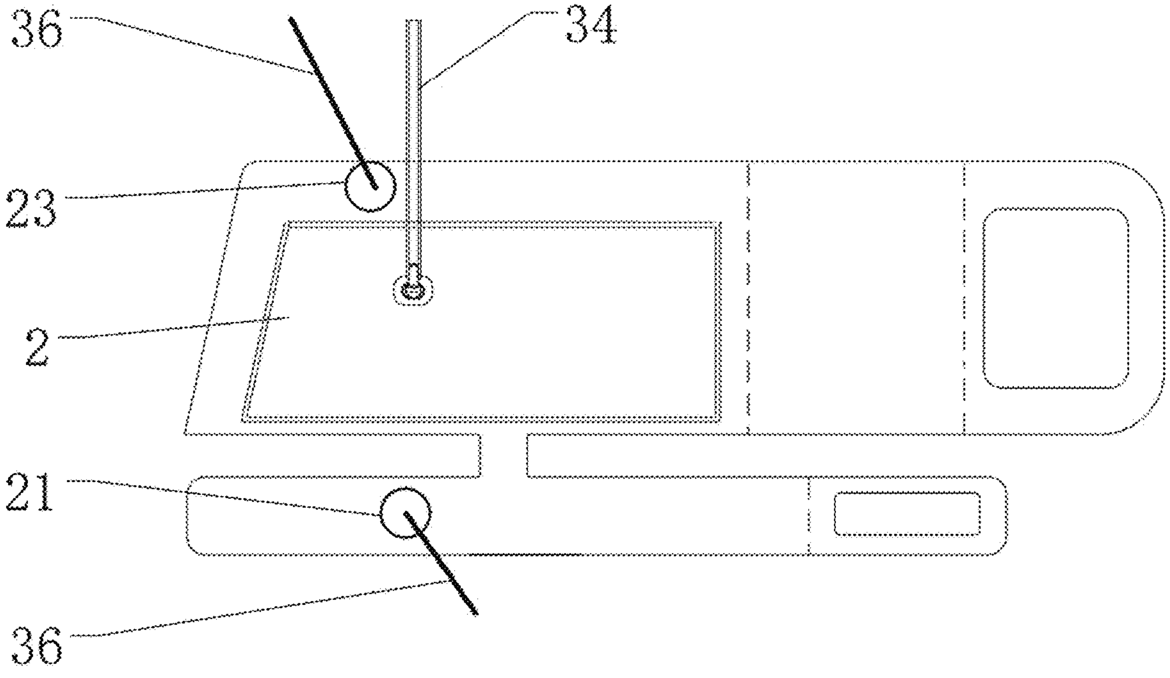
FIG. 14 is a schematic structural diagram of a second type of three-channel pulse wave signal sensor in which pressure sensors or photoelectric sensors are used for the upstream and downstream signal channels.
Figure 15:
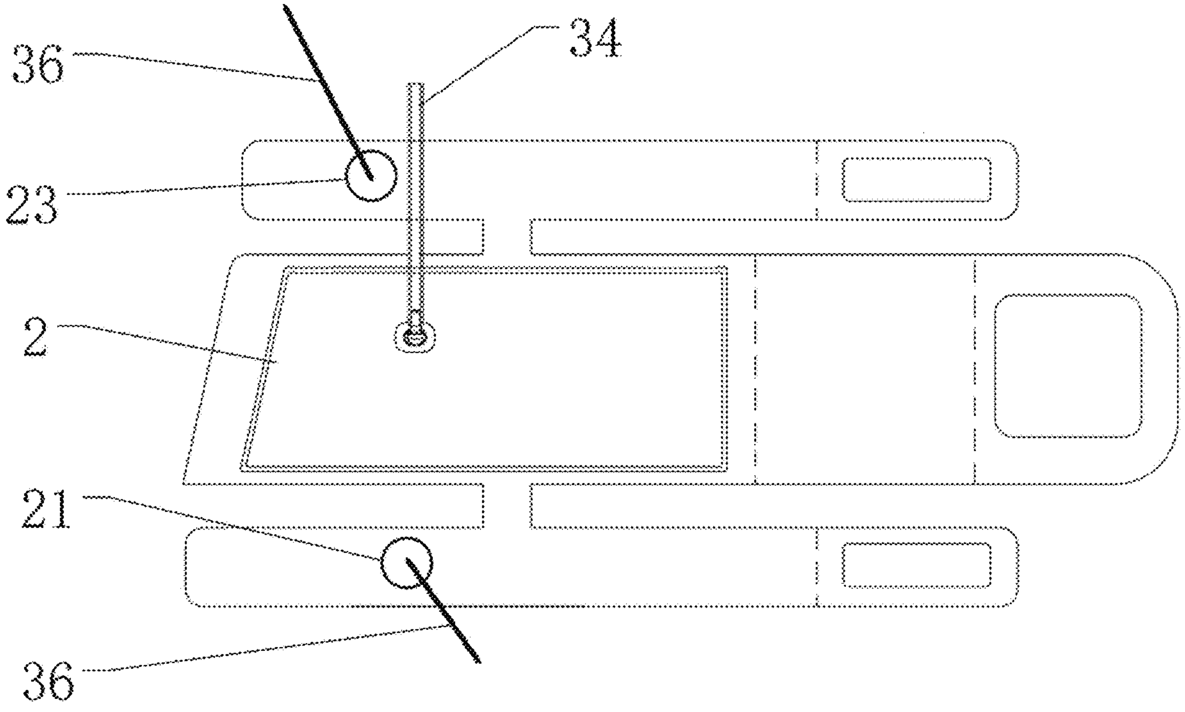
FIG. 15 is a schematic structural diagram of a third type of three-channel pulse wave signal sensor in which pressure sensors or photoelectric sensors are used for the upstream and downstream signal channels.

The structural diagrams of the airbag straps for upstream and downstream pressure sensors are shown in FIGS. 13, 14 and 15. The three signal channels are divided into an upstream electronic signal sensor 21, a midstream airbag strap 2 and a downstream electronic signal sensor 23 according to the blood flow direction. During the measurement, the midstream channel airbag strap 2 can block the arterial blood flow when it is inflated. The width of the airbag of the midstream channel airbag strap 2 is the same as that of the airbag used in the traditional Korotkoff sound method, and the minimum width is determined according to the circumference of the measured limb; for example, the airbag can be classified into three sizes, e.g., a large size, a medium size and a small size. The spacings among the three signal channels, i.e., the upstream electronic signal sensor 21, the midstream airbag strap 2 and the downstream electronic signal sensor 23, are designed according to the length of the measured limb of the subject. The three channels may be closely connected into an integral structure or spaced by certain distances according to the specific requirement of use. As shown in FIGS. 13, 14 and 15, the spacing between the upstream electronic signal sensor 21 and the midstream airbag strap 2 may be between 0 cm and 15 cm, and the spacing between the midstream airbag strap 2 and the downstream electronic signal sensor 23 may be between 0 cm and 30 cm.

Figure 16:
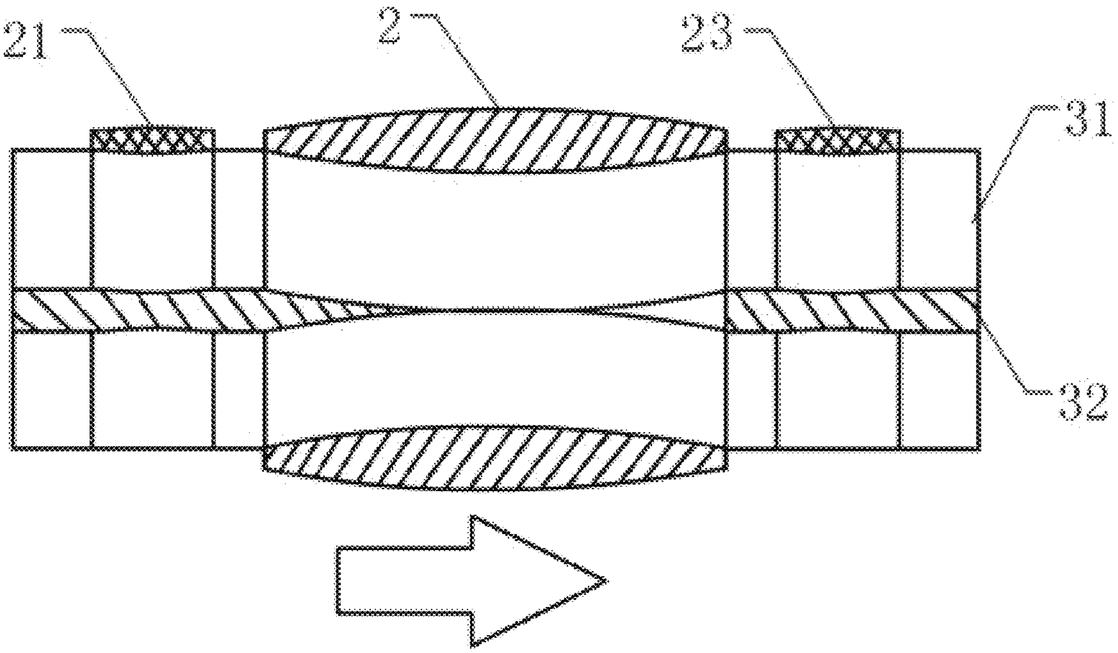
FIG. 16 is a schematic diagram of a system that employs upstream and downstream signal channel sensors and a midstream airbag strap for blocking the blood flow in a brachial artery.

FIG. 16 is a schematic diagram of the midstream airbag strap blocking the blood flow in the brachial artery in the Embodiment 2. The airbag of the midstream airbag strap 2 presses the brachial artery 32 in the upper limb 31, so that the blood flow is stopped and the brachial artery 32 is in a blocked state. The upstream electronic signal sensor 21 and the downstream electronic signal sensor 23 are attached to the skin of the upper limb 31. As shown in the figure, the upstream electronic signal sensor 21 and the downstream electronic signal sensor 23 are fixed to the upper limb 31 by means of a fixing structure, such as a strap body. The upstream electronic signal sensor 21 and the downstream electronic signal sensor 23 may be connected with the midstream airbag strap 2 into an integral structure by means of a strap bracket.

The upstream electronic signal sensor 21 is connected to the signal amplifier 14 through electric wires, the downstream electronic signal sensor 23 is connected to the signal amplifier 15 through electric wires, the midstream airbag strap 2 is connected to the two-way air valve 5 through a tube, and the other end of the two-way air valve 5 is connected to the pressure sensor 12, the air pump 9 and the linear air valve 8 through a tube.

The output terminals of the signal amplifiers 13, 14 and 15 are connected to the input terminals of three analog-to-digital converters (ADCs) of the microprocessor 18 through electric wires. Through calibration with a standard pressure gauge and computation with the microprocessor, the actual pressure values of the upstream, midstream and downstream airbag straps 1, 2 and 3 can be obtained from the signals outputted by the three pressure sensors 10, 11 and 12.

The microprocessor 18 is connected to the display unit 16 and the keyboard 17, and is connected to the two-way air valve 5, the pressure sensor 12, the linear air valve 8 and the air pump 9 through electric wires at the same time.

The built-in inflatable airbag of the upstream signal channel is connected to a corresponding connecting jack on the main unit of the novel non-invasive device for detection of central arterial pressure through an air duct 34, while the pressure sensor of the upstream signal channel and the pressure sensor of the downstream signal channel are respectively connected to two corresponding connection jacks on the main unit of the novel non-invasive device for detection of central arterial pressure through signal connection wires 36.

The measurement process is as follows:

Step 1: Open the two-way air valve 5, close the linear air valve 8, and start the air pump 9 to inflate the midstream airbag strap 2, and acquire and detect the output signal of the signal amplifier 15 connected to the downstream electronic signal sensor 23 at the same time, till the blood flow in the brachial artery is stopped, i.e., the output signal of the signal amplifier 15 is zero; then log the air pressure value of the midstream airbag strap 2 at this moment. Open the two-way air valve 5 further and open the linear air valve 8; in that process, acquire the output signal of the pressure sensor 12 at the same time for monitoring the air pressure of the midstream airbag strap 2, till the air pressure of the midstream airbag strap 2 is greater than the above-mentioned logged air pressure value by several tens of millimeters of mercury, typically 10-100 mmHg; this time zone is a completely blocked time zone $t_x$. Stop the air pump 9 to stop the inflation of the midstream airbag strap 2.

Step 2: Gradually open the linear air valve 8, so that the midstream airbag strap 2 gradually deflates, and, at the same time, acquires the output signals of the signal amplifiers 13, 14 and 15 synchronously as the midstream airbag strap 2 gradually deflates. Acquire and detect the output signal of the signal amplifier 15; pulse wave signals begin to appear gradually, indicating that the blood in the brachial artery begins to flow gradually from the blocked state; this time zone is a semi-blocked time zone ty. In that process, acquire and detect the output signals of the signal amplifiers 13 and 15, so as to obtain the air pressure value of the midstream airbag strap 2 and the amplitudes of the pulse wave signals of the downstream electronic signal sensor 23. Perform linear fitting between the amplitudes of several pulse wave signals initially appearing in the downstream electronic signal sensor 23 and the air pressure of the midstream airbag strap 2 at corresponding pulses, and calculate the air pressure of the midstream airbag strap 2 corresponding to a moment when the amplitude of the pulse wave signal is zero; that air pressure is the systolic pressure of the brachial artery.

Step 3: Gradually open the linear air valve 8 further, so that the midstream airbag strap 2 continues deflating; in that process, acquire and detect the output signals of the signal amplifiers 13 and 15 to obtain pulse wave signal curves of the midstream airbag strap 2 and the downstream electronic signal sensor 23; measure a time delay between the upstrokes in the above two curves, and find out an inflexion point at which the time delay gradually decreases to a constant value; the pressure at that point is the diastolic pressure of the brachial artery.

Step 4: Gradually open the linear air valve 8 and the two-way air valve 5 further, so that the midstream airbag strap 2 gradually deflates to the ambient pressure; now, the measurement is finished.

In this embodiment, the air pressure curves of the upstream and downstream signal channels corresponding to the upstream and downstream channel signal sensors 21 and 23 and the air pressure curve of the midstream airbag strap 2 in the entire measurement process shown in FIG. 8 can also be obtained. The central arterial pressure can be obtained through calculation with the same method as that in the Embodiment 1.

Embodiment 3

From the description of the Embodiment 1 and Embodiment 2, it can be seen that the novel non-invasive device for measuring central arterial pressure in the present invention comprises the three-channel pulse wave signal sensor in the present invention.

As shown in FIGS. 1-7 and 12-16, the three-channel pulse wave signal sensor in the present invention is divided into an upstream signal channel, a midstream signal channel and a downstream signal channel according to the blood flow direction; the upstream signal channel is a strap body 35 with a built-in inflatable airbag or a strap body 35 with an electronic signal sensor attached thereto, the midstream signal channel is a strap body 35 with a built-in inflatable airbag, and the downstream signal channel is a strap body 35 with a built-in inflatable airbag or a strap body 35 with an electronic signal sensor attached thereto, wherein the built-in inflatable airbag of the upstream signal channel, the built-in inflatable airbag of the midstream signal channel and the built-in inflatable airbag of the downstream signal channel are respectively connected to three corresponding connecting jacks on the main unit of a novel non-invasive device for detection of central arterial pressure through air ducts, and the electronic signal sensor of the upstream signal channel and the electronic signal sensor of the downstream signal channel are respectively connected to two corresponding connecting jacks on the main unit of the novel non-invasive device for detection of central arterial pressure through signal connection wires.

Here, it should be noted: the upstream signal channel, the midstream signal channel and the downstream signal channel are divided according to the blood flow direction in the limb. The midstream signal channel is disposed at a position where the signals of the brachial artery in an upper limb or the signals of the femoral artery in a lower limb are measured, and the upstream signal channel and the downstream signal channel are respectively disposed upstream and downstream the midstream signal channel for detecting pulse wave signals, and their positions may be configured by those skilled in the art as required, as long as the object of the present invention can be achieved. Although preferred positions can be provided in the present invention for the positions of the upstream signal channel and the downstream signal channel according to the above description, the positions of the upstream signal channel and the downstream signal channel are not limited to these preferred positions. For example, the downstream signal channel may be disposed at the wrist pulse, such as the artery at the wrist.

More specifically, as shown in FIGS. 1-7, all the upstream, midstream, and downstream signal channels of the three-channel pulse wave signal sensor in the present invention employ airbag straps, including an upstream airbag strap 1, a midstream airbag strap 2, a downstream airbag strap 3, air ducts 34, and a strap body 35. The inflatable airbags of the upstream airbag strap 1, the midstream airbag strap 2 and the downstream airbag strap 3 are respectively connected with an air duct 4, and the three air ducts 4 are respectively connected to three corresponding connecting jacks on the main unit of the novel non-invasive device for detection of central arterial pressure.

According to the length of the measured limb of the subject, the spacings among the three signal channels, namely, the upstream airbag strap 1, the midstream airbag strap 2 and the downstream airbag strap 3, may be classified into three sizes, for example, a large size, a medium size and a small size. The three signal channels may be closely connected into an integral structure or may be fixedly connected at certain distances according to the specific requirement of use. The spacing between the upstream airbag strap 1 and the midstream airbag strap 2 may be between 0 cm and 15 cm, and the spacing between the midstream airbag strap 2 and the downstream airbag strap 3 may be between 0 cm and 30 cm.

When the measurement is made on an upper limb, the downstream airbag strap 3 may be bound below the elbow joint; when the measurement is made on a lower limb, the downstream airbag strap 3 may be bound at a position below the knee joint.

The widths of the upstream and downstream airbag straps should not be too great or too small. If the widths of the upstream and downstream airbag straps are too small, the outputted pressure signals will be too small, and the measurement accuracy will be affected; if the widths of the upstream and downstream airbag straps are too great, the time resolution accuracy will be degraded; besides, limited by the length of the limb of the subject, the widths of the upstream and downstream airbag straps can't be too great. Generally, the widths of the upstream and downstream airbag straps should be 2-3 cm.

In order to ensure the measurement accuracy, the upstream airbag strap 1 should be as close as possible to the position where the upper limb is close to the body, and the upper edge of the midstream airbag strap 2 should be as close as possible to the lower edge of the upstream airbag strap 1, but advantageously the midstream airbag strap and the upstream airbag strap are not connected together completely; otherwise mutual interference between the upstream airbag strap and the midstream airbag strap may occur.

In actual measurement, if the length of the upper limb permits, the upstream, midstream and downstream airbag straps may be placed on the upper limb above the elbow joint at the same time, or the upstream and midstream airbag straps may be placed on the upper limb above the elbow joint, while the downstream airbag strap 3 may be placed below the elbow joint.

The midstream airbag strap 2 can block the arterial blood flow when it is inflated. The width of the airbag of the midstream airbag strap 2 is the same as the width of the airbag strap used in the traditional Korotkoff sound method, and the minimum width is determined according to the circumference of the measured limb of the subject.

The upstream airbag strap 1 is bound and connected to the midstream airbag strap 2, and the midstream airbag strap 2 is fixedly connected to the downstream airbag strap 3, thereby the upstream, midstream and downstream airbags are fixedly mounted on the same strap body 35. During use, the upstream, midstream and downstream airbags are bound to the same measured limb, and their relative positions are kept unchanged in the process of use.

Please see the example of the three-channel pulse wave signal sensor in the present invention, as shown in FIGS. 12-16. Compared with the example shown in FIG. 1-7, the three-channel pulse wave signal sensor in this example employs electronic signal sensors, such as pressure sensors or photoelectric sensors, for the upstream and downstream signal channels, and it employs an airbag strap for the midstream signal channel. The three-channel pulse wave signal sensor in this example comprises an upstream electronic signal sensor strap 21, a midstream airbag strap 2, a downstream electronic signal sensor strap 23, air ducts 34, and a strap body 35, etc.

The upstream electronic signal sensor strap 21 includes an upstream electronic signal sensor, and the downstream electronic signal sensor strap 23 includes a downstream electronic signal sensor; the electronic signal sensors may be pressure sensors or photoelectric sensors, for example. Here, it should be noted: In FIG. 12, for the sake of simplicity, the upstream electronic signal sensor strap 21 and the downstream electronic signal sensor strap 23 in FIG. 12 only schematically show the electronic signal sensors, with the strap body required for the electronic signal sensors omitted. In view that the surface skin and muscles may have slight undulates as a result of the pressure changes in the blood vessels, it is necessary to use a strap body as a binding mechanism to bind the electronic signal sensors to the skin surface with certain pressure during the blood pressure measurement, so as to attain the purpose of measuring the blood pressure accurately.

The inflatable airbag of the midstream airbag strap 2 is connected with an air duct 34, which is connected to a corresponding connecting jack on the main unit of the novel non-invasive device for detection of central arterial pressure and the electronic signal sensors of the upstream electronic signal sensor strap 21 and the downstream electronic signal sensor strap 23 are connected to two corresponding connecting jacks on the main unit of the novel non-invasive device for detection of central arterial pressure through signal connection wires 36 respectively.

According to the length of the measured limb of the subject, the spacings among the three signal channels, namely, the upstream electronic signal sensor strap 21, the midstream airbag strap 2 and the downstream electronic signal sensor strap 23, may be classified into three sizes, for example, a large size, a medium size and a small size. The three signal channels may be closely connected into an integral structure or may be fixedly connected at certain distances, according to the specific requirement of use. The spacing between the upstream electronic signal sensor strap 21 and the edge of the midstream airbag strap 2 may be between 0 cm and 25 cm, preferably between 0 cm and 15 cm, such as 1, 2, 5, or 10 cm, etc.; the spacing between the edge of the midstream airbag strap 2 and the edge of the downstream electronic signal sensor strap 23 may be between 0 cm and 30 cm.

The midstream airbag strap 2 can block the arterial blood flow when it is inflated. The width of the airbag of the midstream airbag strap 2 is the same as the width of the airbag used in the traditional Korotkoff sound method, and the minimum width is determined according to the circumference of the measured limb of the subject.

The upstream electronic signal sensor strap 21 is bound and connected to the midstream airbag strap 2, and the midstream airbag strap 2 is fixedly connected to the downstream electronic signal sensor strap 23, thereby the upstream, midstream and downstream signal channels are fixedly mounted on the same strap body. During use, the upstream, midstream and downstream signal channels are bound to the same measured limb, and their relative positions are kept unchanged in the process of use.

In the case that the upstream and downstream signal channels employ electronic signal sensors, such as pressure sensors or photoelectric sensors, a strap bracket may be used to fix the upstream and downstream pressure sensors or photoelectric sensors, and the midstream airbag strap. The spacings among the upstream, midstream and downstream signal channels and the positions of the upstream, midstream and downstream signal channels are determined by the strap bracket; specifically, the spacing between the edge of the upstream electronic signal sensor and the upper edge of the midstream airbag may be between 0 cm and 15 cm, typically is 1 cm. The spacing between the edge of the downstream electronic signal sensor and the lower edge of the midstream airbag may be between 0 cm and 30 cm, typically is 1 cm.

The fixing bands for fixing the upstream and downstream sensors are fixed on the strap bracket. In the actual measurement application, the tightness of the fixing bands for the upstream and downstream electronic signal sensors is appropriate, so that the upstream and downstream sensors are fixed stationarily on the body surface at the brachial artery in the limb to be measured, without affecting the blood flow.

It should be noted here that only two types of structures as shown in FIGS. 1 and 12 are described for the novel non-invasive device for measuring central arterial pressure and the three-channel pulse wave signal sensor in the embodiments of the present application. However, in fact, both the novel non-invasive device for measuring central arterial pressure and the three-channel pulse wave signal sensor can employ a structure in which one of the upstream signal channel and the downstream signal channel employs an electronic signal sensor. In that case, the signal channel that employs an electronic signal sensor is directly connected to a signal amplifier through electric wires. In such a circumstance, obviously, persons skilled in the art can design the structure between the three signal channels and the microprocessor according to the preceding description of the present application.

Moreover, the present invention can be applied to blood pressure measurement on upper limbs and lower limbs. When blood pressure measurement is made on the upper limbs, the obtained blood pressure is the ascending aortic pressure or the innominate arterial pressure. When blood pressure measurement is made on lower limbs, the obtained blood pressure is the abdominal aortic pressure, more specifically, the blood pressure at the terminal of the abdominal aorta; in that case, the subject should lie flat during the measurement, so that the position of the midstream airbag is essentially at the same level as the abdominal aorta.

While the present invention is further detailed above in some preferred embodiments, the specific implementation of the present invention is not limited to the above description. Persons having ordinary skills in the art can make equivalent replacements or significant variations to the embodiments to achieve the same performance or purpose as the embodiments described above without departing from the inventive concept of the present invention; however, all such replacements or variations shall be deemed as falling into the scope of protection of the present invention as defined by the claims.

What is claimed is:

1. A novel non-invasive method for measuring central arterial pressure and other intraluminal large arterial pressures, wherein the novel non-invasive method utilizes a three-channel pulse wave signal sensor to obtain pulse wave signals, wherein the three-channel pulse wave signal sensor is divided into an upstream signal channel, a midstream signal channel and a downstream signal channel according to a blood flow direction, corresponding to a measured limb; the upstream signal channel is a strap body with a built-in inflatable airbag or an upstream electronic signal sensor, the midstream signal channel is a midstream strap of a strap body with a built-in inflatable airbag, the downstream signal channel is a strap body with a built-in inflatable airbag or a downstream electronic signal sensor, and the measured limb is an upper limb or a lower limb, wherein a spacing between an edge of the upstream signal channel and an edge of the midstream signal channel is within a range of 0 cm to 15 cm; and a spacing between an edge of the midstream signal channel and an edge of the downstream signal channel is within a range of 0 cm to 30 cm, the novel non-invasive method comprising the following steps:

step C: inflating the built-in inflatable airbag of the midstream strap, and acquiring and detecting pulse wave output signals of the upstream and downstream signal channels at the same time, till a blood flow in a brachial artery or femoral artery is stopped, wherein the pulse wave output signal of the downstream signal channel is zero; logging an air pressure value of the built-in inflatable airbag of the midstream strap at this time, inflating the built-in inflatable airbag of the midstream strap further, and monitoring an air pressure of the midstream strap, till the air pressure of the midstream strap is greater than the air pressure value by 10-100 mmHg, and stopping the inflation; at that point, the blood flow in the brachial artery or femoral artery being completely blocked; and acquiring pulse wave output signals of the upstream signal channel for a plurality of heartbeat cycles;

step D: controlling the built-in inflatable airbag of the midstream strap to deflate gradually, and acquiring output signals of the upstream, midstream and downstream signal channels via signal amplifiers synchronously at the same time; as pulse wave signals gradually appear in the downstream signal channel, indicating that blood in the brachial artery or femoral artery gradually begins to flow, the blood flow in the brachial artery or femoral artery being in a semi-blocked state, and the output signals of the upstream, midstream and downstream signal channels being acquired in the process; and determining a moment of an upstroke of the pulse wave signal of the downstream signal channel by acquiring a plurality of pulse wave signals initially appearing in the downstream signal channel, and, at the same time, measuring the air pressure in the built-in inflatable airbag of the midstream signal channel corresponding to the moment of the upstroke to obtain a blood pressure in the brachial artery or femoral artery at a position of the midstream signal channel at the moment; owing to a fact that a blood flow rate is approximately zero at the moment of the upstroke of the pulse wave signal of the downstream signal channel, the blood pressure in the brachial artery or femoral artery at a position of the upstream signal channel being equal to the blood pressure in the brachial artery or femoral artery at the position of the midstream signal channel, wherein the blood pressure in the brachial artery or femoral artery at the position of the upstream signal channel being equal to the air pressure in the built-in inflatable airbag of the midstream strap at that moment;

step E: in the semi-blocked state, logging amplitudes of the plurality of pulse wave signals appearing initially in the downstream signal channel, logging the air pressure in the built-in inflatable airbag of the midstream signal channel at each pulse synchronously, and performing linear fitting between them to calculate a corresponding air pressure in the built-in inflatable airbag of the midstream signal channel when the amplitude of the pulse wave signal of the downstream signal channel crosses zero; that air pressure being a systolic pressure of the brachial artery or femoral artery; as the built-in inflatable airbag of the midstream strap continues deflating, measuring a time delay between an air pressure fluctuation signal of the built-in inflatable airbag of the midstream strap and the pulse wave signal of the downstream signal channel, and performing fitting and calculating a time point when the time delay gradually decreases to a constant value; at that time point, the air pressure of the built-in inflatable airbag of the midstream strap corresponds to a diastolic pressure of the brachial artery or femoral artery, wherein the diastolic pressure of the brachial artery or femoral artery is configured to calculate a systolic pressure of a central artery or other intraluminal aortae; and step F: calculating the systolic pressure and diastolic pressure of the central artery or other intraluminal aortae, according to the pulse wave signals of the upstream and downstream signal channels, an air pressure signal of the built-in inflatable airbag of the midstream strap and the diastolic pressure of the brachial artery or femoral artery that are acquired synchronously in the above process; and measurement is finished;

wherein a maximum value of the blood pressure in the brachial artery or femoral artery in a completely blocked state is obtained according to a delayed time point in the completely blocked state, the blood pressure in the brachial artery or femoral artery at the position of the upstream signal channel, and a pulse wave signal curve of the upstream signal channel for the plurality of heartbeat cycles in the completely blocked state, which is acquired in step C; the maximum value of the blood pressure in the brachial artery or femoral artery in the completely blocked state is approximately equal to the systolic pressure of the central artery or other intraluminal aortae; and near a diastolic pressure point, the blood flow rate in the brachial artery or femoral artery is approximately zero; wherein the diastolic pressure measured at a position of the brachial artery or femoral artery is approximately equal to the diastolic pressure of central artery or other intraluminal aortae.

2. The novel non-invasive method according to claim 1, wherein in the step D:

a second derivative of an air pressure fluctuation curve of the built-in inflatable airbag of the midstream signal channel in the semi-blocked state is calculated, and a first zero-crossing point from positive to negative, wherein a zero-crossing point of blood flow acceleration, is found out; the blood pressure in the brachial artery or femoral artery at the position of the upstream signal channel at a moment of the zero-crossing point of blood flow acceleration in the semi-blocked state is calculated according to the pulse wave signal curve of the upstream signal channel at this moment and the blood pressure in the brachial artery at the position of the upstream signal channel at the moment of the upstroke of the pulse wave signal of the downstream signal channel in the semi-blocked state; and a delay time between a pulse upstroke and the zero-crossing point of blood flow acceleration in the semi-blocked state is calculated for a heartbeat cycle of the pressure curve of the built-in inflatable airbag of the midstream signal channel; a corresponding delay time point in the completely blocked state is determined for a heartbeat cycle of the pulse wave signal curve of the upstream signal channel; the blood pressure in the brachial artery or femoral artery at the position of the upstream signal channel at that delay time point in the completely blocked state is approximately equal to the blood pressure in the brachial artery or femoral artery the position of the upstream signal channel at the same delay time point in the semi-blocked state, wherein the delay time from the pulse upstroke to this point is the same as the above-mentioned delay time.

3. The novel non-invasive method according to claim 1, wherein in the measurement process, the built-in inflatable airbag of the midstream strap is kept at the same level as an intraluminal large artery to be measured, when a left arm is to be measured, the intraluminal large artery is an ascending aorta; when a right arm is to be measured, the intraluminal large artery is an innominate artery; and when a lower limb is to be measured, the intraluminal large artery is a terminal of an abdominal aorta.

4. The novel non-invasive method according to claim 1, wherein the inflatable airbag of the midstream strap is connected to a first end of a two-way air valve through a tube, and a second end of the two-way air valve is connected to a pressure sensor, an air pump and a linear air valve through a tube; in the step C, the midstream strap is inflated by opening the two-way air valve, closing the linear air valve, and starting the air pump; and in the step D, the midstream strap is controlled to deflate gradually by opening the two-way air valve connected to the inflatable airbag of the midstream strap and gradually opening the linear air valve.

5. The novel non-invasive method according to claim 1, wherein both the upstream signal channel and the downstream signal channel are strap bodies with built-in inflatable airbags, and the inflatable airbag of the upstream signal channel is connected to a first end of a first two-way air valve through a tube, and is connected to a first pressure sensor through a tube at the same time; the inflatable airbag of the midstream signal channel is connected to a first end of a second two-way air valve through a tube, and is connected to a microporous air valve through a tube at the same time, and the microporous air valve is connected to the inflatable airbag of the downstream signal channel through a tube; the inflatable airbag of the downstream signal channel is connected to a first end of a third two-way air valve through a tube, and is connected to a second pressure sensor and the microporous air valve through a tube at the same time; second ends of the three two-way air valves are connected together through a tube and is connected to a third pressure sensor, an air pump and a linear air valve through a tube, and the first, second and third pressure sensors are respectively connected to first, second and third signal amplifiers through electric wires, wherein the novel non-invasive method further comprises the following step B before the step C: starting the air pump to inflate the inflatable airbag of the upstream signal channel to tens of millimeters of mercury via the two-way air valve of the upstream signal channel, and synchronously acquiring pulse wave signals of the upstream and downstream signal channels and air pressure signals of the inflatable airbag of the midstream signal channel, till the measurement is finished; and the step C is: opening the two-way air valve connected to the inflatable airbag of the midstream signal channel, and gradually opening the linear air valve, wherein the inflatable airbag of the midstream signal channel gradually deflates, the blood in the brachial artery or femoral artery gradually begins to flow, and pulse wave signals begin to appear in the downstream signal channel; a current state being a semi-blocked state; logging the amplitudes of the plurality of pulse wave signals appearing initially in the downstream signal channel, logging the air pressure in the inflatable airbag of the midstream signal channel at each pulse synchronously, and performing linear fitting between them to calculate a corresponding air pressure in the inflatable airbag of the midstream signal channel when the amplitude of the pulse wave signal of the downstream signal channel crosses zero; that air pressure being the systolic pressure of the brachial artery or femoral artery; as the inflatable airbag of the midstream signal channel continues deflating, measuring a time delay between the air pressure fluctuation signal of the inflatable airbag of the midstream signal channel and the pulse wave signal of the downstream signal channel, and performing fitting and calculating a time point when the time delay gradually decreases to a constant value; at that moment, the pressure of the inflatable airbag of the midstream signal channel being the diastolic pressure of the brachial artery or femoral artery.

6. The novel non-invasive method according to claim 5, further comprising the following step A before the step B: opening the two-way air valve connected to the inflatable airbag of the midstream signal channel, closing the linear air valve, and starting the air pump to inflate the inflatable airbag of the midstream signal channel via the two-way air valve and inflate the inflatable airbag of the downstream signal channel via the microporous air valve, and acquiring and detecting the air pressure fluctuation signal of the inflatable airbag of the downstream signal channel at the same time, till the blood flow in the brachial artery or femoral artery is stopped, wherein the pulse wave signal of the inflatable airbag of the downstream signal channel is zero; opening the two-way air valve connected to the inflatable airbag of the midstream signal channel, and gradually opening the linear air valve, wherein the inflatable airbag of the midstream signal channel gradually deflates, the blood in the brachial artery or femoral artery gradually begins to flow, and pulse wave signals begin to appear in the downstream signal channel; logging the amplitudes of the plurality of pulse wave signals initially appearing in the downstream signal channel, and logging the air pressure of the inflatable airbag of the midstream signal channel at each pulse synchronously, performing linear fitting between them, and calculating the air pressure of the inflatable airbag of the midstream signal channel corresponding to the moment when the amplitude of the pulse wave signal of the downstream signal channel crosses zero; that air pressure being the systolic pressure of the brachial artery or femoral artery; as the inflatable airbag of the midstream signal channel continues deflating, measuring a time delay between the air pressure fluctuation signal of the inflatable airbag of the midstream signal channel and the pulse wave signal of the downstream signal channel, and performing fitting and calculating a time point when the time delay gradually decreases to a constant value; at that moment, the pressure of the inflatable airbag of the midstream signal channel being the diastolic pressure of the brachial artery or femoral artery; and "inflating the inflatable airbag of the upstream signal channel via the two-way valve of the upstream signal channel to tens of millimeters of mercury" in the step B means "inflating the inflatable airbag of the upstream signal channel via the two-way valve of the upstream signal channel to the diastolic pressure of the brachial artery or femoral artery obtained in the step A".

7. A novel non-invasive device for measuring central arterial pressure and other intraluminal large arterial pressure, comprising:

a three channel pulse wave signal sensor, wherein the three-channel pulse wave signal sensor is divided into an upstream signal channel, a midstream signal channel and a downstream signal channel in a blood flow direction, corresponding to a measured limb; the upstream signal channel, the midstream signal channel and the downstream signal channel are respectively fixed upstream, midstream and downstream in the blood flow direction during blood pressure measurement, the upstream signal channel is a strap body with a built-in inflatable airbag or an upstream electronic signal sensor, the midstream signal channel is a midstream strap in a strap body with a built-in inflatable airbag, and the downstream signal channel is a strap body with a built-in inflatable airbag or a downstream electronic signal sensor; wherein the built-in inflatable airbag of the upstream signal channel, the built-in inflatable airbag of the midstream signal channel and the built-in inflatable airbag of the downstream signal channel are respectively connected to the main unit of a non-invasive device for measuring blood pressure through air ducts, wherein blood vessel pressure signals are transmitted; and the upstream electronic signal sensor and the downstream electronic signal sensor respectively transmit upstream and downstream pulse wave signals of blood flow to the main unit of the non-invasive device for measuring blood pressure, wherein a spacing between an edge of the upstream signal channel and an edge of the midstream signal channel is within a range of 0 cm to 15 cm; and a spacing between an edge of the midstream signal channel and an edge of the downstream signal channel is within a range of 0 cm to 30 cm;

a main unit comprising a microprocessor;

wherein all of the upstream signal channel, the midstream signal channel and the downstream signal channel of the three-channel pulse wave signal sensor are strap bodies with built-in inflatable airbags;

the built-in inflatable airbag of the upstream signal channel is connected to a first end of a first two-way air valve through a tube, and is connected to a first pressure sensor through a tube at the same time;

the built-in airbag of the midstream signal channel is connected to a first end of a second two-way air valve through a tube, and is connected to a first end of a microporous air valve through a tube at the same time, and a second end of the microporous air valve is connected to the built-in inflatable airbag of the downstream signal channel through a tube;

the built-in inflatable airbag of the downstream signal channel is connected to a third two-way air valve through a tube, and is connected to a third pressure sensor and the second end of the microporous air valve through a tube at the same time;

the second ends of the first, second and third two-way air valves are connected together through tubes, and are connected to a second pressure sensor, an air pump and a linear air valve through tubes;

the first, second and third pressure sensors are respectively connected to first, second and third signal amplifiers through electric wires, and output terminals of the first, second and third signal amplifiers are connected to input terminals of three analog-to-digital converters (ADCs) of the microprocessor through electric wires;

the microprocessor is connected to the first, second and third two-way air valves, the first, second and third signal pressure sensors, the linear air valve and the air pump through electric wires; and wherein the microprocessor is configured to control the novel non-invasive device to operate the following steps:

step B: starting the air pump to inflate the inflatable airbag of the upstream signal channel to tens of millimeters of mercury via the two-way air valve of the upstream signal channel, and synchronously acquiring pulse wave signals of the upstream and downstream signal channels and air pressure signals of the inflatable airbag of the midstream signal channel, till the measurement is finished;

step C: opening the second two-way air valve connected to the inflatable airbag of the mid stream signal channel, and gradually opening the linear air valve, wherein the inflatable airbag of the midstream signal channel gradually deflates, the blood in the brachial artery or femoral artery gradually begins to flow, and pulse wave signals begin to appear in the downstream signal channel; a current state being a semi-blocked state; logging the amplitudes of the plurality of pulse wave signals appearing initially in the downstream signal channel, logging the air pressure in the inflatable airbag of the midstream signal channel at each pulse synchronously, and performing linear fitting between them to calculate a corresponding air pressure in the inflatable airbag of the midstream signal channel when the amplitude of the pulse wave signal of the downstream signal channel crosses zero; that air pressure being the systolic pressure of the brachial artery or femoral artery; as the inflatable airbag of the midstream signal channel continues deflating, measuring a time delay between the air pressure fluctuation signal of the inflatable airbag of the midstream signal channel and the pulse wave signal of the downstream signal channel, and performing fitting and calculating a time point when the time delay gradually decreases to a constant value; at that moment, the pressure of the inflatable airbag of the midstream signal channel being the diastolic pressure of the brachial artery or femoral artery;

step D: controlling the built-in inflatable airbag of the midstream strap to deflate gradually, and acquiring output signals of the upstream, midstream and downstream signal channels via signal amplifiers synchronously at the same time; as pulse wave signals gradually appear in the downstream signal channel, indicating that blood in the brachial artery or femoral artery gradually begins to flow, the blood flow in the brachial artery or femoral artery being in a semi-blocked state, and the output signals of the upstream, midstream and downstream signal channels being acquired in the process; and determining a moment of an up stroke of the pulse wave signal of the downstream signal channel by acquiring a plurality of pulse wave signals initially appearing in the downstream signal channel, and, at the same time, measuring the air pressure in the built-in inflatable airbag of the midstream signal channel corresponding to the moment of the upstroke to obtain a blood pressure in the brachial artery or femoral artery at a position of the midstream signal channel at the moment; owing to a fact that a blood flow rate is approximately zero at the moment of the upstroke of the pulse wave signal of the downstream signal channel, the blood pressure in the brachial artery or femoral artery at a position of the upstream signal channel being equal to the blood pressure in the brachial artery or femoral artery at the position of the midstream signal channel, wherein the blood pressure in the brachial artery or femoral artery at the position of the upstream signal channel being equal to the air pressure in the built-in inflatable airbag of the midstream strap at that moment;

step E: in the semi-blocked state, logging amplitudes of the plurality of pulse wave signals appearing initially in the downstream signal channel, logging the air pressure in the built-in inflatable airbag of the midstream signal channel at each pulse synchronously, and performing linear fitting between them to calculate a corresponding air pressure in the built-in inflatable airbag of the midstream signal channel when the amplitude of the pulse wave signal of the downstream signal channel crosses zero; that air pressure being a systolic pressure of the brachial artery or femoral artery; as the built-in inflatable airbag of the midstream strap continues deflating, measuring a time delay between an air pressure fluctuation signal of the built-in inflatable airbag of the midstream strap and the pulse wave signal of the downstream signal channel, and performing fitting and calculating a time point when the time delay gradually decreases to a constant value; at that time point, the air pressure of the built-in inflatable airbag of the mid stream strap corresponds to a diastolic pressure of the brachial artery or femoral artery, wherein the diastolic pressure of the brachial artery or femoral artery is configured to calculate a systolic pressure of a central artery or other intraluminal aortae; and step F: calculating the systolic pressure and diastolic pressure of the central artery or other intraluminal aortae, according to the pulse wave signals of the upstream and downstream signal channels, an air pressure signal of the built-in inflatable airbag of the midstream strap and the diastolic pressure of the brachial artery or femoral artery that are acquired synchronously in the above process; and measurement is finished;

wherein a maximum value of the blood pressure in the brachial artery or femoral artery in the completely blocked state is obtained according to a delayed time point in the completely blocked state, the blood pressure in the brachial artery or femoral artery at the position of the upstream signal channel, and a pulse wave signal curve of the upstream signal channel for the plurality of heartbeat cycles in the completely blocked state, which is acquired in step C; the maximum value of the blood pressure in the brachial artery or femoral artery in the completely blocked state is approximately equal to the systolic pressure of the central artery or other intraluminal aortae; and near a diastolic pressure point, the blood flow rate in the brachial artery or femoral artery is approximately zero; wherein the diastolic pressure measured at a position of the brachial artery or femoral artery is approximately equal to the diastolic pressure of central artery or other intraluminal aortae.

8. A novel non-invasive device for measuring central arterial pressure and other intraluminal large arterial pressure, comprising:

a three channel pulse wave signal sensor, wherein the three-channel pulse wave signal sensor is divided into an upstream signal channel, a midstream signal channel and a downstream signal channel in a blood flow direction, corresponding to a measured limb; the upstream signal channel, the midstream signal channel and the downstream signal channel are respectively fixed upstream, midstream and downstream in the blood flow direction during blood pressure measurement, the upstream signal channel is a strap body with a built-in inflatable airbag or an upstream electronic signal sensor, the midstream signal channel is a midstream strap in a strap body with a built-in inflatable airbag, and the downstream signal channel is a strap body with a built-in inflatable airbag or a downstream electronic signal sensor; wherein the built-in inflatable airbag of the upstream signal channel, the built-in inflatable airbag of the midstream signal channel and the built-in inflatable airbag of the downstream signal channel are respectively connected to the main unit of a non-invasive device for measuring blood pressure through air ducts, wherein blood vessel pressure signals are transmitted; and the upstream electronic signal sensor and the downstream electronic signal sensor respectively transmit upstream and downstream pulse wave signals of blood flow to the main unit of the non-invasive device for measuring blood pressure, wherein a spacing between an edge of the upstream signal channel and an edge of the midstream signal channel is within a range of 0 cm to 15 cm; and a spacing between an edge of the midstream signal channel and an edge of the downstream signal channel is within a range of 0 cm to 30 cm;

a main unit comprising a microprocessor;

wherein the upstream signal channel of the three-channel pulse wave signal sensor is an upstream electronic signal sensor, and the downstream signal channel is a downstream electronic signal sensor;

the upstream electronic signal sensor is connected to a first signal amplifier through electric wires;

the built-in inflatable airbag of the midstream signal channel is connected to a first end of a two-way air valve through a tube, and a second end of the two-way air valve is connected to a pressure sensor, an air pump and a linear air valve through a tube, and the pressure sensor is connected to a second signal amplifier through electric wires;

the downstream electronic signal sensor is connected to a third signal amplifier through electric wires;

output terminals of the first, second and third signal amplifiers are connected to input terminals of three analog to digital converters (ADCs) of the microprocessor through electric wires; and the microprocessor is connected to the two-way air valves, signal pressure sensors, a linear air valve and an air pump through electric wires, wherein the processor is configured to control the novel non-invasive device to operate the following steps:

step C: opening the two-way air valve, closing the linear air valve, and opening the air pump to inflate the built-in inflatable airbag of the midstream strap, and acquiring and detecting pulse wave output signals of the upstream and downstream signal channels at the same time, till a blood flow in a brachial artery or femoral artery is stopped, wherein the pulse wave output signal of the downstream signal channel is zero; logging an air pressure value of the built-in inflatable airbag of the midstream strap at this time, inflating the built-in inflatable airbag of the midstream strap further, and monitoring an air pressure of the midstream strap, till the air pressure of the midstream strap is greater than the air pressure value by 10-100 mmHg, and stopping the inflation; at that point, the blood flow in the brachial artery or femoral artery being completely blocked; and acquiring pulse wave output signals of the upstream signal channel for a plurality of heartbeat cycles;

step D: opening the linear air valve to control the built-in inflatable airbag of the midstream strap to deflate gradually, and acquiring output signals of the upstream, midstream and downstream signal channels via signal amplifiers synchronously at the same time; as pulse wave signals gradually appear in the downstream signal channel, indicating that blood in the brachial artery or femoral artery gradually begins to flow, the blood flow in the brachial artery or femoral artery being in a semi-blocked state, and the output signals of the upstream, midstream and downstream signal channels being acquired in the process; and determining a moment of an upstroke of the pulse wave signal of the downstream signal channel by acquiring a plurality of pulse wave signals initially appearing in the downstream signal channel, and, at the same time, measuring the air pressure in the built-in inflatable airbag of the midstream signal channel corresponding to the moment of the upstroke to obtain a blood pressure in the brachial artery or femoral artery at a position of the midstream signal channel at the moment; owing to a fact that a blood flow rate is approximately zero at the moment of the upstroke of the pulse wave signal of the downstream signal channel, the blood pressure in the brachial artery or femoral artery at a position of the upstream signal channel being equal to the blood pressure in the brachial artery or femoral artery at the position of the midstream signal channel, wherein the blood pressure in the brachial artery or femoral artery at the position of the upstream signal channel being equal to the air pressure in the built-in inflatable airbag of the midstream strap at that moment;

step E: in the semi-blocked state, logging amplitudes of the plurality of pulse wave signals appearing initially in the downstream signal channel, logging the air pressure in the built-in inflatable airbag of the midstream signal channel at each pulse synchronously, and performing linear fitting between them to calculate a corresponding air pressure in the built-in inflatable airbag of the midstream signal channel when the amplitude of the pulse wave signal of the downstream signal channel crosses zero; that air pressure being a systolic pressure of the brachial artery or femoral artery; as the built-in inflatable airbag of the midstream strap continues deflating, measuring a time delay between an air pressure fluctuation signal of the built-in inflatable airbag of the midstream strap and the pulse wave signal of the downstream signal channel, and performing fitting and calculating a time point when the time delay gradually decreases to a constant value; at that time point, the air pressure of the built-in inflatable airbag of the midstream strap corresponds to a diastolic pressure of the brachial artery or femoral artery, wherein the diastolic pressure of the brachial artery or femoral artery is configured to calculate a systolic pressure of a central artery or other intraluminal aortae; and step F: calculating the systolic pressure and diastolic pressure of the central artery or other intraluminal aortae, according to the pulse wave signals of the upstream and downstream signal channels, an air pressure signal of the built-in inflatable airbag of the midstream strap and the diastolic pressure of the brachial artery or femoral artery that are acquired synchronously in the above process; and the measurement is finished;

wherein a maximum value of the blood pressure in the brachial artery or femoral artery in a completely blocked state is obtained according to a delayed time point in the completely blocked state, the blood pressure in the brachial artery or femoral artery at the position of the upstream signal channel, and a pulse wave signal curve of the upstream signal channel for the plurality of heartbeat cycles in the completely blocked state, which is acquired in step C; the maximum value of the blood pressure in the brachial artery or femoral artery in the completely blocked state is approximately equal to the systolic pressure of the central artery or other intraluminal aortae; and near a diastolic pressure point, the blood flow rate in the brachial artery or femoral artery is approximately zero; wherein the diastolic pressure measured at a position of the brachial artery or femoral artery is approximately equal to the diastolic pressure of central artery or other intraluminal aortae.

9. The novel non-invasive device according to claim 7, wherein the microprocessor calculates as follows:

(I): in a semi-blocked time zone $t_y$, the downstream signal channel begins to generate pulse wave signals; the air pressure in a midstream blocking airbag at the moment time $t_I$ of the upstroke of the pulse wave signal is the blood pressure in the brachial artery at the time $t_I$, at the time $t_I$, when a width of the midstream blocking airbag is sufficient, the blood pressure in the brachial artery at the position of the midstream signal channel is approximately equal to the air pressure in the midstream blocking airbag and the following equation (1) is satisfied:

$$P_{2I} = H_{2I} \tag{1}$$

(II): the lateral pressure $P_{2I}$ of the blood on the brachial artery at the position of the upstream signal channel at the time $t_I$ is calculated according to a blood pressure $P_{1I}$ in the brachial artery at the position of the built-in inflatable airbag of the midstream strap at the time $t_I$;

during the measurement, the blood flow in the brachial artery is blocked after the built-in inflatable airbag of the midstream strap is inflated and pressurized; at this time, the blood pressure $P_{2I}$ in the brachial artery at the position of the built-in inflatable airbag of the midstream strap satisfies the following equation (2):

$$P_{2I} = P_C - \rho a_I L_2 \tag{2}$$

in equation (2), $P_C$ is the central arterial pressure, $a_I$ is an acceleration of the blood flow at the time $t_I$, $L_2$ is a length of a blood vessel from a junction between one end of a left subclavian artery and an ascending aorta to the built-in inflatable airbag of the midstream strap, and ρ is a density of the blood;

the inflatable airbag of the upstream signal channel only appropriately pressurizes the measured limb and feels a brachial arterial pulse wave at the position of the upstream signal channel but does not block the blood flow, wherein at the position of the upstream signal channel at the time $t_I$, the lateral pressure $P_{1I}$ of the blood in the brachial artery on the blood vessel of the brachial artery satisfies the following equation (3):

$$P_{1I} = P_C - \rho a_I L_1 - \frac{1}{2}\rho V_I^2 \tag{3}$$

in expression (3), $V_I$ is the blood flow rate in the brachial artery at the time $t_I$, and $L_1$ is the length of the blood vessel from the junction between one end of the left subclavian artery and the ascending aorta to the upstream signal channel;

at the time $t_I$, the blood flow rate in the brachial artery is approximately 0, wherein $V_I \approx 0$, and, in the measurement, the upstream signal channel is as close as possible to the built-in inflatable airbag of the midstream strap, wherein it is allowed to be deemed that $L_1 \approx L_2$; and the following equation is allowed to be obtained according to equations (2) and (3):

$$P_{1I} = P_{2I} - \rho a(L_1 - L_2) - \frac{1}{2}\rho V_I^2 \approx P_{2I} \tag{4}$$

the following equation is allowed to be obtained according to equations (1) and (4):

$$P_{1I} = H_{2I} \tag{5}$$

wherein the blood pressure in the brachial artery at the position of the upstream signal channel at the time $t_I$ is equal to the air pressure in the airbag at the time $t_I$;

(III): a blood pressure $P_{1II}$ in the brachial artery at time $t_{II}$ is calculated, according to a pressure curve of the upstream signal channel in a pulse cycle where time $t_I$ is located in a time zone $t_x$ and the blood pressure $P_{1I}$ in the brachial artery at the position of the upstream signal channel at the time $t_I$;

owing to a fact that a degree of pressurization of an upstream signal channel sensor on the brachial artery, comprising the air pressure in the upstream airbag, is constant in the semi-blocked time zone $t_y$, a proportional relationship between a signal intensity of the air pressure in the upstream airbag and the blood pressure in the brachial artery remains unchanged in the heartbeat cycle where time $t_I$ is located;

wherein the following equation (6) is satisfied:

$$\frac{(P_{1II} - P_d)}{(H_{1II} - H_d)} = \frac{(P_{1I} - P_d)}{(H_{1I} - H_d)} \tag{6}$$

the following equation is obtained:

$$P_{1II} = \frac{(P_{1I} - P_d)(H_{1II} - H_d)}{(H_{1I} - H_d)} + P_d \tag{7}$$

(IV): a blood pressure $P_{1III}$ din the brachial artery at the position of the upstream signal channel at time $t_{III}$ in the completely blocked time zone $t_x$ is calculated, according to the blood pressure $P_{1II}$ in the brachial artery at the position of the upstream signal channel at the time $t_{II}$ in the semi-blocked time zone $t_y$;

according to a definition of the time $t_{II}$, the acceleration a of the blood movement in the brachial artery at this moment is a=0, at the time $t_{II}$, the blood pressure $P_{1II}$ in the brachial artery at the position of the upstream signal channel satisfies the following equation (8):

$$P_{1II} = P_{CII} - \rho a L_1 - \frac{1}{2}\rho V^2 = P_{CII} - \frac{1}{2}\rho V_{II}^2 \tag{8}$$

where $V_{II}$ is the blood flow rate in the brachial artery at the time $t_{II}$;

since the brachial artery is partially blocked and the blood flow rate in the brachial artery is much lower than a maximum blood flow rate in a completely open state at the time $t_{II}$, the following result is allowed to be obtained:

$$P_{1II} = P_{CII} - \Delta P \approx P_{CII} \tag{9}$$

at the time $t_{III}$, since the blood flow rate and acceleration in the brachial artery are close to zero because current time is in the completely blocked time zone $t_x$, and:

$$V_{III} \approx 0,\ a_{III} \approx 0$$

where $V_{III}$ is the blood flow rate in the brachial artery at the time $t_{III}$, and $a_{III}$ is the blood flow acceleration at the time $t_{III}$;

$$P_{1III} = P_{CIII} - \rho a_{III} L_1 - \frac{1}{2}\rho V_{III}^2 \approx P_{CIII} \tag{10}$$

in short-time measurement, it can be deemed that the central arterial pressure and a rising edge of its waveform remain unchanged; wherein for the heartbeat cycle where the time $t_{II}$ and the time $t_{III}$ are located, when pulse upstroke time points are $t_{xC}$ and $t_{yC}$ respectively, and:

$$P_C|_{(t_{xC}+t)} = P_C|_{(t_{yC}+t)}$$

where t is any time interval smaller than a heartbeat cycle;

wherein since delay time Δt of the pulse upstroke at the time $t_{II}$ is the same as the delay time Δt of the pulse upstroke at the time $t_{III}$, the following formula (11) is satisfied:

$$P_{CII} = P_{CIII} \tag{11}$$

the following equation is allowed to be obtained from equations (9), (10) and (11):

$$P_{1III} = P_{1\,II} \tag{12}$$

(V): a maximum value $P_{1s}$ of the blood pressure in the brachial artery at the position of the upstream signal channel is calculated, according to the pressure curve of the upstream signal channel in the heartbeat cycle where time $t_{III}$ is located and the blood pressure $P_{1III}$ in the brachial artery at the position of the upstream signal channel at the time $t_{III}$ and the systolic pressure $P_{cs}$ of the central artery is obtained approximately;

owing to the fact that the blood flow rate and acceleration in the brachial artery are close to zero in the completely blocked time zone $t_x$, and a measuring airbag is kept at the same level as the ascending aorta during the measurement, the systolic pressure of the central artery is approximately equal to the maximum value $P_{1s}$ of the blood pressure in the brachial artery at the position of the upstream signal channel, wherein $P_{CS} \approx P_{1s}$;

owing to the fact that the degree of pressurization of the upstream signal channel sensor on the brachial artery or the air pressure in the upstream airbag is constant in the completely blocked time zone $t_x$, the proportional relationship between the signal intensity of the air pressure in the upstream airbag and the blood pressure in the brachial artery remains unchanged in the heartbeat cycle where the time $t_{III}$ is located;

$$\frac{(P_{1s} - P_d)}{(H_{1s} - H_d)} = \frac{(P_{1III} - P_d)}{(H_{1III} - H_d)} \tag{13}$$

the following equation is allowed to be obtained from the equations (5), (7), (12), and (13):

$$P_{1s} = \frac{(P_{1III} - P_d)(H_{1s} - H_d)}{(H_{1III} - H_d)} + P_d = \frac{(P_{1II} - P_d)(H_{1s} - H_d)}{(H_{1III} - H_d)} + P_d = \frac{(H_{2\,I} - P_d)(H_{1\,II} - H_d)(H_{1s} - H_d)}{(H_{1\,I} - H_d)(H_{1III} - H_d)} + P_d \tag{14}$$

$$P_{cs} = P_{1s}. \tag{15}$$

10. The novel non-invasive device according to claim 8, wherein the microprocessor calculates as follows:

(I): in a semi-blocked time zone $t_y$, the downstream signal sensor begins to generate pulse wave signals; the air pressure in a midstream blocking airbag at the moment time $t_I$ of the upstroke of the pulse wave signal is the blood pressure in the brachial artery at the time $t_I$, at the time $t_I$, when a width of the midstream blocking airbag is sufficient, the blood pressure in the brachial artery at the position of the midstream signal channel is approximately equal to the air pressure in the midstream blocking airbag and the following equation (1) is satisfied:

$$P_{2I} = H_{2I} \tag{1}$$

(II): the lateral pressure $P_{2I}$ of the blood on the brachial artery at the position of the upstream signal channel at the time $t_I$ is calculated according to a blood pressure $P_{1I}$ in the brachial artery at the position of the built-in inflatable airbag of the midstream strap at the time $t_I$;

during the measurement, the blood flow in the brachial artery is blocked after the built-in inflatable airbag of the midstream strap is inflated and pressurized; at this time, the blood pressure $P_{2I}$ in the brachial artery at the position of the built-in inflatable airbag of the midstream strap satisfies the following equation (2):

$$P_{2I} = P_C - \rho a_I L_2 \tag{2}$$

in equation (2), $P_C$ is the central arterial pressure, $a_I$ is an acceleration of the blood flow at the time $t_I$, $L_2$ is a length of a blood vessel from a junction between one end of a left subclavian artery and an ascending aorta to the built-in inflatable airbag of the midstream strap, and ρ is a density of the blood;

the sensor of the upstream signal channel only appropriately pressurizes the measured limb and feels a brachial arterial pulse wave at the position of the upstream signal channel but does not block the blood flow, wherein at the position of the upstream signal channel at the time $t_I$, the lateral pressure $P_{1I}$ of the blood in the brachial artery on the blood vessel of the brachial artery satisfies the following equation (3):

$$P_{1I} = P_C - \rho a_I L_1 - \frac{1}{2}\rho V_I^2 \tag{3}$$

in expression (3), $V_I$ is the blood flow rate in the brachial artery at the time $t_I$, and $L_1$ is the length of the blood vessel from the junction between one end of the left subclavian artery and the ascending aorta to the upstream signal channel;

at the time $t_I$, the blood flow rate in the brachial artery is approximately 0, wherein $V_I \approx 0$, and, in the measurement, the upstream signal channel is as close as possible to the built-in inflatable airbag of the midstream strap, wherein it is allowed to be deemed that $L_1 \approx L_2$; and the following equation is allowed to be obtained according to equations (2) and (3):

$$P_{1I} = P_{2I} - \rho a(L_1 - L_2) - \frac{1}{2}\rho V_I^2 \approx P_{2I} \tag{4}$$

the following equation is allowed to be obtained according to equations (1) and (4):

$$P_{1I} = H_{2I} \quad (5)$$

wherein the blood pressure in the brachial artery at the position of the upstream signal channel at the time $t_I$ is equal to the air pressure in the airbag at the time $t_I$;

(III): a blood pressure $P_{1II}$ in the brachial artery at time $t_{II}$ is calculated, according to a pressure curve of the upstream signal channel in a pulse cycle where time $t_I$ is located in a time zone $t_x$ and the blood pressure $P_{1I}$ in the brachial artery at the position of the upstream signal channel at the time $t_I$;

owing to a fact that a degree of pressurization of an upstream signal channel sensor on the brachial artery, comprising the air pressure in the upstream airbag, is constant in the semi-blocked time zone $t_y$, a proportional relationship between a signal intensity of the upstream signal channel sensor and the blood pressure in the brachial artery remains unchanged in the heartbeat cycle where time $t_I$ is located;

wherein the following equation (6) is satisfied:

$$\frac{(P_{1II} - P_d)}{(H_{1II} - H_d)} = \frac{(P_{1I} - P_d)}{(H_{1I} - H_d)} \quad (6)$$

the following equation is obtained:

$$P_{1II} = \frac{(P_{1I} - P_d)(H_{1II} - H_d)}{(H_{1I} - H_d)} + P_d \quad (7)$$

(IV): a blood pressure $P_{1III}$ in the brachial artery at the position of the upstream signal channel at time $t_{III}$ in the completely blocked time zone $t_x$ is calculated, according to the blood pressure $P_{1II}$ in the brachial artery at the position of the upstream signal channel at the time $t_{II}$ in the semi-blocked time zone $t_y$;

according to a definition of the time $t_{II}$, the acceleration a of the blood movement in the brachial artery at this moment is a=0, at the time $t_{II}$, the blood pressure $P_{1II}$ in the brachial artery at the position of the upstream signal channel satisfies the following equation (8):

$$P_{1II} = P_{CII} - \rho a L_1 - \frac{1}{2}\rho V^2 = P_{CII} - \frac{1}{2}\rho V_{II}^2 \quad (8)$$

where $V_{II}$ is the blood flow rate in the brachial artery at the time $t_{II}$;

since the brachial artery is partially blocked and the blood flow rate in the brachial artery is much lower than a maximum blood flow rate in a completely open state at the time $t_{II}$, the following result is allowed to be obtained:

$$P_{1II} = P_{CII} - \Delta P \approx P_{CII} \quad (9)$$

at the time $t_{III}$, since the blood flow rate and acceleration in the brachial artery are close to zero because current time is in the completely blocked time zone $t_x$, and:

$$V_{III} \approx 0,\ a_{III} \approx 0$$

where $V_{III}$ is the blood flow rate in the brachial artery at the time $t_{III}$, and $a_{III}$ is the blood flow acceleration at the time $t_{III}$;

$$P_{1III} = P_{CIII} - \rho a_{III} L_1 - \frac{1}{2}\rho V_{III}^2 \approx P_{CIII} \quad (10)$$

in short-time measurement, it can be deemed that the central arterial pressure and a rising edge of its waveform remain unchanged; wherein for the heartbeat cycle where the time $t_{II}$ and the time $t_{III}$ are located, when pulse upstroke time points are $t_{xC}$ and $t_{yC}$ respectively, and:

$$P_C|_{(t_{xC}+t)} = P_C|_{(t_{yC}+t)}$$

where t is any time interval smaller than a heartbeat cycle;

wherein since delay time Δt of the pulse upstroke at the time $t_{II}$ is the same as the delay time Δt of the pulse upstroke at the time $t_{III}$, the following formula (11) is satisfied:

$$P_{CII} = P_{CIII} \quad (11)$$

the following equation is allowed to be obtained from equations (9), (10) and (11):

$$P_{1III} = P_{1II} \quad (12)$$

(V): a maximum value $P_{1s}$ of the blood pressure in the brachial artery at the position of the upstream signal channel is calculated, according to the pressure curve of the upstream signal channel in the heartbeat cycle where time $t_{III}$ is located and the blood pressure $P_{1III}$ in the brachial artery at the position of the upstream signal channel at the time $t_{III}$ and the systolic pressure $P_{cs}$ of the central artery is obtained approximately;

owing to the fact that the blood flow rate and acceleration in the brachial artery are close to zero in the completely blocked time zone $t_x$, and a measuring airbag is kept at the same level as the ascending aorta during the measurement, the systolic pressure of the central artery is approximately equal to the maximum value $P_{1s}$ of the blood pressure in the brachial artery at the position of the upstream signal channel, wherein $P_{CS} \approx P_{1s}$;

owing to the fact that the degree of pressurization of the upstream signal channel sensor on the brachial artery or the air pressure in the upstream airbag is constant in the completely blocked time zone $t_x$, the proportional relationship between the signal intensity of the upstream signal channel and the blood pressure in the brachial artery remains unchanged in the heartbeat cycle where the time $t_{III}$ is located;

$$\frac{(P_{1s}-P_d)}{(H_{1s}-H_d)}=\frac{(P_{1III}-P_d)}{(H_{1III}-H_d)} \tag{13}$$

the following equation is allowed to be obtained from the equations (5), (7), (12), and (13):

$$P_{1s}=\frac{(P_{1II}-P_d)(H_{1s}-H_d)}{(H_{1III}-H_d)}=\frac{(P_{1III}-P_d)(H_{1s}-H_d)}{(H_{1III}-H_d)}+P_d+P_d=\frac{(H_{2I}-P_d)(H_{1II}-H_d)(H_{1s}-H_d)}{(H_{1I}-H_d)(H_{1III}-H_d)}+P_d \tag{14}$$

$$P_{cs}=P_{1s}. \tag{15}$$

* * * * *